United States Patent
Yocum et al.

(10) Patent No.: US 11,072,807 B2
(45) Date of Patent: Jul. 27, 2021

(54) PRODUCTION OF ORGANIC ACIDS BY FERMENTATION OF GENETICALLY ENGINEERED YEAST CELLS AT LOW PH

(71) Applicant: PTT GLOBAL CHEMICAL PUBLIC COMPANY LIMITED, Bangkok (TH)

(72) Inventors: R. Rogers Yocum, Lexington, MA (US); Sudhanshu Dole, North Andover, MA (US); Janice G. Pero, Lexington, MA (US)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 0 days.

(21) Appl. No.: 14/428,202

(22) PCT Filed: Sep. 13, 2013

(86) PCT No.: PCT/US2013/059828
§ 371 (c)(1),
(2) Date: Mar. 13, 2015

(87) PCT Pub. No.: WO2014/043591
PCT Pub. Date: Mar. 20, 2014

(65) Prior Publication Data
US 2015/0240270 A1   Aug. 27, 2015

Related U.S. Application Data

(60) Provisional application No. 61/701,293, filed on Sep. 14, 2012.

(51) Int. Cl.
| | | |
|---|---|---|
| *C12P 7/46* | (2006.01) | |
| *C12P 7/56* | (2006.01) | |
| *C12N 15/52* | (2006.01) | |
| *C12N 15/81* | (2006.01) | |
| *C12N 9/02* | (2006.01) | |
| *C12N 9/12* | (2006.01) | |
| *C12N 9/00* | (2006.01) | |
| *C12N 9/88* | (2006.01) | |
| *C12N 9/04* | (2006.01) | |
| *C12N 1/14* | (2006.01) | |
| *C12N 9/10* | (2006.01) | |

(52) U.S. Cl.
CPC .................. *C12P 7/46* (2013.01); *C12N 1/14* (2013.01); *C12N 9/001* (2013.01); *C12N 9/0006* (2013.01); *C12N 9/0008* (2013.01); *C12N 9/1025* (2013.01); *C12N 9/12* (2013.01); *C12N 9/88* (2013.01); *C12N 9/93* (2013.01); *C12N 15/52* (2013.01); *C12N 15/81* (2013.01); *C12P 7/56* (2013.01)

(58) Field of Classification Search
None
See application file for complete search history.

(56) References Cited

U.S. PATENT DOCUMENTS

| | | | | |
|---|---|---|---|---|
| 2012/0040422 | A1* | 2/2012 | Jansen | C12P 7/46 435/145 |
| 2012/0225461 | A1* | 9/2012 | Dole | C12N 9/1025 435/145 |

FOREIGN PATENT DOCUMENTS

| | | | |
|---|---|---|---|
| WO | WO2007030830 | * | 3/2007 |
| WO | WO 2010115067 | * | 7/2010 |
| WO | WO2012103261 | * | 2/2012 |

OTHER PUBLICATIONS

Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
Abbott et al. FEMS Yeast Res. Dec. 2009;9(8):1123-36.*
Camarasa et al. Yeast. May 2007;24(5):391-401.*

* cited by examiner

*Primary Examiner* — Christian L Fronda
(74) *Attorney, Agent, or Firm* — Oblon, McClelland, Maier & Neustadt, L.L.P.

(57) ABSTRACT

This invention relates to the biosynthesis of organic acids in genetically modified microorganisms. More specifically, this invention provides genetically modified microorganisms that are particularly tolerant to organic acids at low pH and are capable of producing organic acids by fermentation at low pH.

24 Claims, 5 Drawing Sheets
Specification includes a Sequence Listing.

PRODUCTION OF ORGANIC ACIDS BY FERMENTATION OF GENETICALLY ENGINEERED YEAST CELLS AT LOW PH

CROSS-REFERENCE TO RELATED APPLICATIONS

The application is the U.S. national stage application of International Patent Application No. PCT/US2013/059828, filed on Sep. 13, 2013 which claims the priority of the U.S. Provisional Application Ser. No. 61/701,293 filed on Sep. 14, 2012.

FIELD OF THE INVENTION

The present invention is in the field of producing renewable chemical feedstocks using biocatalysts that have been genetically engineered to increase their ability to convert renewable carbon resources into useful compounds. More specifically, the present invention provides a process for producing organic acids, such as succinic acid, fumaric acid, malic acid, and lactic acid from renewable carbon resources using genetically modified biocatalysts.

BACKGROUND OF THE INVENTION

Succinic acid (also referred to herein as "succinate" for brevity) is a potentially large volume chemical used already, or potentially used, in the manufacture of various products, including animal feed, plasticizers, congealers, polymers, fibers, and plastics, most notably polybutyl succinate (also known as "polybutylene succinate", "poly (butylene succinate)" and "PBS"). Many of the polymers made from succinate are biodegradable at a much faster rate than other polymers derived from petroleum such as polyethylene, polypropylene, polystyrene, and polyethylene terephthalate (PET). As such, plastics made from succinate are highly desirable, since they will decay more quickly in landfills or other composting environments (Kunioka et al., 2009). This property extends to many other polymers and plastics where the monomeric subunits are biologically derived compounds or their chemical equivalent, rather than petrochemically derived compounds that are not normally found abundantly in living organisms. For example, polymers derived from fumaric acid (fumarate), malic acid (malate), adipic acid (adipate), L-lactic acid (L-lactate), D-lactic acid (D-lactate), and other naturally occurring organic acids, are all degraded more readily than many petrochemically derived polymers in composting environments. As such, for the benefit of humanity, it is desirable to replace polymers and plastics currently made from petrochemicals with polymers and plastics made from biochemicals (chemicals made and/or metabolized by living organisms).

Of course many biochemicals, such as succinate, fumarate, and adipate, can be manufactured from petroleum, and in fact, the currently used processes (as of 2012) for making PBS and nylons use petroleum-derived monomers. However, since the world's petroleum supply is finite, it would also be desirable to develop materials and methods for producing biochemical monomers by fermentation from renewable carbon sources such as sugars, sugar polymers, glycerol, fatty acids, carbon dioxide, lignin, or any other form of biomass or waste derived from biomass. Thus it is desirable to develop processes for manufacturing biodegradable plastics from biorenewable resources.

Several processes have been developed for producing organic acids by fermentation, for example production of L-lactic acid by bacteria of the genera *Lactobacillus*, *Escherichia*, and *Bacillus* (Grabar et al., 2006; Patel et al., 2006), production of fumaric acid by the filamentous fungus *Rhizopus oryzea* (Roa Engel et al., 2008), D-lactic acid by a genetically engineered *Escherichia coli* or *Bacillus coagulans* (Wang et al., 2011; Jarboe et al., 2010; Grabar et al., 2006), muconic acid by a genetically engineered *E. coli* (Niu et al., 2002), L-lactic acid by various genetically engineered yeast species of the genera *Saccharomyces*, *Kluyveromyces*, *Candida*, and *Issatchenkia* (Zhang et al., 2011; U.S. Pat. Nos. 7,049,108, 7,229,805), malic acid by genetically engineered *Saccharomyces cerevisiae* (US 2008/0090273), and succinic acid by genetically engineered *E. coli*, *Saccharomyces cerevisiae*, *Issatchenkia orientalis*, and *Yarrowia lipolytica* (Zhang et al., 2009a; Zhang et al 2009b; Jantama et al., 2008a; Jantama et al, 2008b; WO 2010/003728; WO 2008/128522; WO 2010/043197; WO 2012/103261; US2012/0015415).

Many of the above mentioned processes, including all of those based on bacteria, use organisms that cannot grow at low pH. As used in this invention, the term "low pH" is defined as a pH of 5.6 or lower. When a low-pH intolerant biocatalyst such as a bacterial biocatalyst is used in the production of organic acids such as succinic acid, the pH of the culture medium becomes acidic and the culture medium is maintained at a pH from about 5.6 to about 7.5 by addition of base, usually a hydroxide, carbonate, bicarbonate, or a mixture thereof, of sodium, potassium, ammonium, magnesium, or calcium. As a result, the organic acid in the culture broth exists as a salt, and the majority of the organic acid molecules are charged. The charged state presents an advantage and a disadvantage. The advantage is that the charged salt does not easily diffuse back across the cell membrane(s) into the cell. The disadvantage is that the polymerization chemistry or other further chemical use of the organic acid usually requires the protonated form (also called the "free acid") of the organic acid, so that the salts produced by fermentation require potentially costly downstream processing to provide the free acid form. As such, it would be advantageous to produce organic acids at low pH (a pH near or, more preferably, below that of the lowest pKa of the organic acid), such that a majority of the molecules are in the free acid state. Other considerations aside, a low pH fermentation broth should be less expensive to process to give a pure preparation of the free acid, since much less counterion (such as sodium, potassium, ammonium, magnesium, calcium) would have to be separated. However, a problem with this approach, at least in theory, is that the protonated acids are more hydrophobic than their respective salts, so the protonated acids are much more prone to diffuse back into the cell through the hydrophobic lipid bilayer of the cell membrane (van Maris et al., 2004). If energy is needed to pump the organic acid out of the cell, then a futile cycle ensues, which would deplete the cell's resources away from the desired biosynthesis (van Maris et al., 2004).

Nonetheless, there exist processes for producing organic acids by fermentation at low pH. The best known and oldest is the process for producing citric acid by *Aspergillus niger* and related species (Papagianni, 2007), although citric acid might be a special case in that the protonated form might be more polar than that of mono- and dicarboxylic acids. Recently, processes have been developed for producing L-lactic acid by various yeasts at low pH, and one of these yeasts has been implemented commercially, although it has not been revealed which one (Aker et al., Session Abstract 170, Society for Industrial Microbiology Annual Meeting, Jul. 24-28, 2011, New Orleans, La., USA). *Saccharomyces*

*cerevisiae* strains have been engineered to produce malate, but the pH was maintained at 5 (Zelle et al., 2008). Even more recently, *Saccharomyces cerevisiae, Issatchemkia orientalis*, and *Yarrowia lipolytica* strains have been genetically engineered to produce succinic acid at relatively low pH (WO 2008/128522; WO 2010/043197; US 2012/0040422; WO 2010/003728; WO 2011/023700; WO 2009/101180; WO 2012/038390; WO 2012/103261; and US 2012/0015415). However, the titers and yields, when mentioned, that have been published in these prior art patent applications are relatively low compared to those obtained by bacterial production systems operating at neutral pH, so it is not obvious that the titers and yields from the published yeast processes are high enough to be competitive with a neutral pH bacterial process (Jantama et al 2008a; Jantama et al., 2008b). Furthermore, as is disclosed in the instant invention, there are several yeast strains isolated from rotting bagasse and other environments that are more tolerant to succinic acid and L-lactic acid at low pH than strains of *Saccharomyces cerevisiae*.

WO 2012/103261 discloses strains of *Issatchenkia orientalis* that have been engineered to produce succinate or malate. These strains were derived from a wild type parent that was chosen as being the most resistant to high concentrations of succinate at low pH among a collection of many different yeast species. In particular, the *I. orientalis* strain chosen was more resistant to succinate when compared to a *Kluyveromyces marxianus* strain. WO 2012/103261 does not disclose yeasts of the genus *Kluyveromyces* engineered to overproduce succinate. However, as will be disclosed herein, the instant inventors have discovered a new wild type strain of *Kluyveromyces marxianus* that is more tolerant to succinate at low pH than an *I. orientalis* strain when grown in a dilute rich medium (see FIG. 1). Thus, there is clearly some variability among different strains within a species with respect to tolerance to organic acids at low pH, and the precise conditions under which the screening is done might influence the outcome of such screens. For example, the screening for tolerance to succinate in WO 2012/103261 that identified *I. orientalis* as the most tolerant to succinate was done presumably in a YPD medium (with 2% glucose as a carbon source), at pH 2.5, while the screening disclosed herein below that identified a wild *K. marxianus* strain, that is not identical to any known strain of *K. marxianus*, as the most succinate tolerant strain was done in a ¼strength YP medium (2.5 g/l yeast extract plus 5 g/l peptone) with 5% glucose and a starting pH of 3.3. WO 2012/103261 discloses that deletion of the PCK gene encoding PEP carboxykinase is beneficial for succinate production because PEP carboxykinase is usually considered to be a gluconeogenic enzyme, and as such works in the opposite of the desired direction. However, in an appropriately engineered strain, the instant inventors propose the exact opposite, namely that using PEP carboxykinase for the anapleurotic (carbon dioxide incorporation) reaction is more favorable than use of pyruvate carboxylase or PEP carboxylase as claimed in WO 2012/103261. The inventors of WO 2012/103261 propose that reducing equivalents for the reductive pathway to succinate be provided by increasing flux through the pentose phosphate pathway. In contrast, the instant inventors submit that the reducing equivalents for succinate synthesis are best provided by balancing flux through the oxidative and reductive branches of the TCA cycle.

Strains of *Issatchenkia orientalis* have been disclosed that have been engineered to produce malate or fumarate (WO 2012/103263). However, WO 2012/103263 does not disclose use of *Kluyveromyces* as a host for malate or fumarate production, and, as above for WO 2012/103261, it teaches against using PEP carboxykinase for the carboxylation reaction from PEP to oxaloacetate (OAA).

In any case, the succinate production parameters disclosed in WO 2102/103261 and the malate production parameters disclosed in WO 2012/103263 are not attractive enough for commercial production of succinate or malate, respectively, so there is still room for improvement, and there is still a need to develop improved processes for producing succinic acid and other organic acids, such as fumaric acid, L-malic acid, D-lactic acid, L-lactic acid by fermentation at low pH.

*Saccharomyces cerevisiae* naturally produces a significant amount of succinic acid when grown aerobically or anaerobically on glucose as a carbon source (Oura, 1977; Heerde and Radler, 1978; de Klerck, 2010). The oxidative and reductive biochemical pathways to succinate in *Saccharomyces* are well known (de Klerck, 2010) and are similar to those of *E. coli* and many other organisms, except that in yeasts, many of the oxidative steps are predominantly catalyzed inside the mitochondria or promitochondria (also known as protomitochindria). Succinic acid is an intermediate in the Kreb's cycle, also known as the tricarboxylic acid cycle or TCA cycle. Under conditions where oxygen is present, most aerobic organisms run the TCA cycle oxidatively, starting with oxaloacetate (OAA) and acetyl-CoA, running through citrate, aconitate, isocitrate, alpha-ketoglutarate, succinyl-CoA, succinate, fumarate, malate, and back to OAA. In the process, reducing equivalents in the form of NADH, NADPH, and $FADH_2$ are produced, along with 2 moles of $CO_2$ per mole of acetyl-CoA. Thus, the acetyl portion of acetyl-CoA is in effect oxidized to $CO_2$ and water in the cycle, and OAA acts as a primer or catalyst that gets regenerated. Succinate is an intermediate. Under aerobic conditions, the reducing equivalents are oxidized ultimately by oxygen to produce water and ATP by oxidative phosphorylation, and as a result, NAD, NADP, and FAD are regenerated for the next cycle. However, in the absence of oxygen or other oxidizing agent, the TCA cycle cannot run exclusively in the above described oxidative cycle, because the cell has no way to regenerate the quantity of NAD, NADP, and FAD that is required by the TCA cycle. Since at least three of the TCA cycle intermediates, α-ketoglutarate, succinyl-CoA, and OAA are nonetheless needed as biochemical intermediates for other biosynthetic pathways, under anaerobic conditions in minimal media, most of the enzymatic reactions of the TCA cycle must still be active. Under these conditions, the TCA "cycle" is split into two linear, non-cyclic forks or branches, an oxidative branch that begins as described above, but which ends at succinyl-CoA, and a reductive branch that also begins with OAA, but runs in the opposite direction of that described above, through malate and fumarate, ending with succinate. This first branch shall be referred herein as the oxidative branch, and the second branch shall be referred to herein as the reductive branch of the TCA cycle, since as one of the pathways to succinate from OAA, it consumes reducing equivalents as NADH and $FADH_2$ to regenerate NAD and FAD.

As defined in this present invention, the term "oxidative pathway for succinate production" or "oxidative branch" of the TCA cycle refers to the portion of the Kreb's cycle that starts with phosphoenol pyruvate and ends in succinate and include intermediates such as oxaloacetate, acetyl-CoA, citrate, aconitate, isocitrate, alpha-ketoglutarate and succinyl-CoA and involves the production of reducing equivalents such as NADH. On the other hand, as defined in this present invention, the term "reductive pathway for succinate production" or "reductive branch" of the TCA cycle refers to the portion of the Kreb's cycle that starts with oxaloacetate and ends in succinate including malate and fumarate as the intermediated and consumes reducing equivalents such as NADH and $FADH_2$. In a wild type yeast cell, the Kreb's cycle operates entirely within the mitochondria. The instant invention relates to a genetically engineered yeast cell wherein the oxidative pathway for succinate production and reductive pathway for succinate production operate entirely within the cytoplasm.

Oxaloacetate is produced in the cytoplasm of the yeast cell through a carboxylation reaction of either pyruvate of phosphoenolpyruvate. Carboxylation of pyruvate to oxaloacetate is mediated by pyruvate carboxylase while the carboxylation of phosphoenolpyruvae is mediated either by phosphoenol pyruvate carboxylase or phosphoenol pyruvate carboxykinase. Oxaloaceate enters from the cytoplasm into the mitochondria and initiates the Kreb's cycle.

The carbon from isocitric acid, an intermediate in the oxidative part of the Kreb's cycle also enters into the glyoxylate cycle with the resultant formation of glyoxylate and succinic acid in the cytoplasm. The glyoxlate cycle is also known in the art as the glyoxylate shunt. The glyoxylate pathway branches off from citric acid cycle within the mitochondria and results in the production of succinic acid as an end product in the cytoplasm. Efforts have been made to exploit the glyoxylate pathway in succinic acid production. In order to accumulate succinic acid in the cytoplasm through the operation of glyoxylate cycle, one has to achieve the following three genetic manipulations: (i) block the operation of citric acid cycle at appropriate location so that the carbon from citric acid cycle is redirected into the glyoxylate cycle; (ii) enhance the operation of enzymes involved in the glyoxylate cycle; and (iii) prevent the reentry of succinic acid from cytosol into the mitochondria by means of removing the dicarboxylic acid transporter in the mitochondrial envelop through genetic manipulations.

The objective of the present invention is to produce succinic acid outside of mitochondria without the involvement of glyoxylate cycle. This is achieved by means of expressing within the cytoplasm of yeast cells those enzymes which are usually expressed inside the mitochondria and are involved either in the oxidative or reductive part of the Kreb's cycle.

E. coli strains have been genetically engineered to produce succinate under anaerobic or microaerobic conditions (Jantama et al., 2008a; Jantama et al., 2008b). Theoretically, in order to achieve the highest possible yields of succinate from glucose, succinate must be synthesized by both the oxidative and the reductive branches of the TCA cycle (WO2011/063157). The reductive pathway is inherently higher yielding from glucose than the oxidative pathway, because the reductive pathway does not lose any carbon atoms, and it incorporates a carbon atom from carbon dioxide in the PEP carboxykinase reaction. However, since the reductive pathway requires one NADH and one $FADH_2$ per succinate, and since the glycolytic pathway from glucose to PEP generates just one NADH per 3-carbon unit, the reductive pathway from glucose to succinate is not redox balanced, and therefore cannot operate by itself anaerobically. The oxidative pathway produces two NADH and one NADPH per 3-carbon unit (as pyruvate) consumed. Therefore, if both the reductive and oxidative pathways operate at the correct ratio, then production and consumption of redox equivalents (as NADH, NADPH, and $FADH_2$) can be balanced, even in the absence of oxygen.

In E. coli, and probably in most or all other organisms that operate a TCA cycle, the regulation of the TCA has most likely evolved to conserve carbon and energy, and not to maximize yield of succinate from glucose. As such, E. coli strains that were engineered for homofermentative succinate production were subjected to a "re-evolution" (also referred as metabolic evolution) that presumably resulted in balancing the two branches of the TCA cycle to provide redox balance under anaerobic or microaerobic conditions (Jantama et al., 2008a; Jantama et al., 2008b).

Despite the theoretical advantage of producing dicarboxylic acids, such as succinic acid, in low pH fermentations with yeasts, due to subcellular compartmentalization in the form of membrane-bound organelles in yeasts, engineering succinate production in yeast is not nearly as straight forward as in E. coli. First, in Saccharomyces, and probably in most, if not all, other yeasts, under aerobic conditions, the TCA cycle operates inside the mitochondria or promitochondria (WO 2008/128522, WO 2010/043197). In the absence of specific succinate transporters, the mitochondrial inner membrane is impermeable to succinate (Lee et al., 2011), but transporters are known that import succinate into the mitochondria in exchange for fumarate or phosphate (Lee et al., 2011; Palmieri et al., 1999; Palmieri et al., 2000). However, there are no known mechanisms for secreting succinate from the mitochondria to the cytoplasm, so that succinate produced from the TCA cycle, even in a branched mode, would not be easily secreted outside of the mitochondria and hence outside of the cell. As such, it was recognized in the prior art that it would be desirable to engineer biosynthesis of dicarboxylic acids such as malate and succinate in the cytoplasm, by arranging for key enzymes in the reductive pathway to malate and succinate, such as pyruvate carboxylase, malate dehydrogenase, and fumarase, to be present and sufficiently active in the cytoplasm, outside of the mitochondria (US 2008/0090273, US 2012/0040422, WO 2010/003728, WO 2011/023700. WO 2009/101180, and WO 2012/038390, WO 2008/128522, WO 2010/043197, WO 2009/011974). However, the prior art has not recognized or addressed the problem of how to export succinate from the mitochondria or how to attain redox balance under anaerobic or microaerobic conditions, while maximizing succinate yield from glucose (or other carbon source) in yeast.

Two mitochondrial membrane proteins are reported to pump succinate into the mitochondria in yeast (Lee et al., 2011; Palmieri et al., 1999; Palmieri et al., 2000) in exchange for phosphate or fumarate. As such, in a preferred embodiment of this invention, either or both of the genes encoding those transporters, namely DIC1 (WO 2007/128522) and SFC1, would be deleted from yeast strains, in combination with the novel features of yeasts of this invention that are engineered to produce succinate.

Prior art references using either yeast or bacteria for succinate production rely on use of the glyoxylate shunt to produce reducing equivalents (as NADH) to supply the reductive succinate pathway (WO 2009/101180, WO 2008/128522, Vemuri et al., 2002; Cox et al., 2006; Zhu et al., 2013). Furthermore, since the glyoxylate shunt enzymes isocitrate lyase and malate synthase are cytoplasmic in yeasts, use of these enzymes is relied upon to synthesize succinate in the cytoplasm of yeast (WO 2009/101180, WO 2008/128522). However, use of the glyoxylate shunt for succinate synthesis in either bacteria or yeast is inherently less efficient for the cell when compared to use of the oxidative branch of the TCA cycle, because the oxidative branch of the TCA cycle produces an ATP or GTP at the succinyl-CoA to succinate step, while the glyoxylate shunt does not produce an ATP or GTP at any step. Thus, use of the glyoxylate shunt is wasteful, so it is advantageous to avoid its use for biosynthesis of succinate and other dicarbaoxylic acids, TCA cycle intermediates, and derivatives thereof. The instant inventors have recognized the importance of having both the reductive and oxidative branches of the TCA cycle operating for succinate production, and in yeast, it is desirable to have both branches operating in the cytoplasm, and to avoid using the glyoxylate shunt enzymes. To this end, the genes that encode isocitrate lyase (for example, ScICL1, ScICL2, KmICL1, IoILC1, and others) and malate synthase (for example ScMLS1, ScMLS2, KmMLS1, IoMLS1, and others) can be deleted from host yeast strains by well known methods in the art.

In particular, although the concept of balancing reductive and oxidative pathways for succinate production is discussed in the prior art (Jantama et al., 2008b; Abbott et al., 2009) none of the prior art references suggest redirecting the enzymes of the oxidative branch of the TCA cycle from the mitochondria to the cytoplasm in yeast, or directly installing enzymes of the oxidative succinate pathway, for example bacterial enzymes that have no mitochondrial directing signal sequences, in the cytoplasm. In fact, the prior art teaches against use of the oxidative branch of the TCA cycle for dicarboxylic acid production in yeast by recommending the deletion of RTG3, a gene that encodes a positive regulator of TCA enzymes that operate in the oxidative direction (WO 2009/011974)), and the prior art that discusses balancing a reductive and oxidative route recommends use of the glyoxylate shunt instead of the TCA enzymes for the oxidative route (Raab and Lang, 2011). Moreover, the regulation of the production and activities of all of the relevant enzymes, both inside and outside the mitochondria, is extremely complicated, and it is not obvious how to engineer appropriate levels. Finally, the mitochondrial membrane is not permeable to NAD and NADH, and it is not obvious how to attain efficient redox balance between the mitochondrial matrix and the cytoplasm. There are at least three systems that are potentially useful for shuttling reducing equivalents across the mitochondrial membrane, namely the asparate-malate shuttle, the glycerol-3-phosphate dehydrogenase shuttle, and an alcohol dehydrogenase shuttle (Easlon et al., 2008). However, again, it is not obvious how to engineer one or more of these shuttles to create desirable conditions for biosynthesis of succinate or other dicarboxylic acids. The invention disclosed herein recognizes these problems and provides solutions to these problems.

Prior art researchers have disclosed materials and methods for producing L-lactate and D-lactate in various yeasts, including yeasts from the genera *Saccharomyes, Kluyveromyces, Candida, Torulopsis, Zygosaccharomyces*, and *Issatchenkia* (Zhang et al., 2011; U.S. Pat. Nos. 6,429,006, 7,049,108, 7,326,550, 7,229,805, and US Patent Application Publications 2009/0226989, 2007/0031950). However, the biosynthetic pathway from glucose to lactate is inherently much simpler than pathways to succinate. The glucose to lactate pathway is redox balanced, and it does not involve the mitochondria, so the prior art on lactate biosynthesis in yeast is not sufficient to teach how to best produce succinate or other dicarboxylic acids in yeast. Several prior art disclosures teach methods and materials for producing succinate in *Saccharomyces cerevisiae*. However, *S. cerevisiae* is not as tolerant to organic acids at low pH as are some yeasts of other genera, such as *Kluyveromyce, Pichia, Hansenula, Candida* and *Issatchenkia*, so it would be an improvement to be able to produce succinate in non-*Saccharomyces* yeasts.

In addition to the tolerance to organic acids, there are many other fundamental differences between the *Saccharomyces* yeasts and other yeasts such as *Kluyveromyces* and *Issatchenkia*. Therefore, the teachings of the prior art do not render it obvious how to engineer non-*Saccharomyces* yeast species for economically viable succinate production without undue experimentation. For example, while wild type *S. cerevisiae* contains at least three active isozymes of pyruvate decarboxylase, encoded by ScPDC1, ScPDC5, and ScPDC6, wild type *Kluyveromyces lactis* and wild type *K. marxianus* each contains only one active pyruvate decarboxylase, encoded by KlPDC1 and KmPDC1, respectively. Secondly, the regulation of gene expression in *K. lactis* can be quite different from that in *S. cerevisiae* (Booth et al., 2010; Rusche and Rine, 2010). Thirdly, the default case for *S. cerevisiae* is diploidy. Diploids are stable and sporulate only when starved. However, the default case for *K. lactis* is haploidy. *K. lactis* haploids only mate when they are starved, and the resulting diploids sporulate to haploids as soon as mating occurs (Booth et al., 2010; Kegel et al., 2006). Fourth, *K. lactis* and *K. marxianus* exhibit much higher levels of non-homologous end joining than *S. cerevisiae* (Kegel et al., 2006; Abdel-Banat et al., 2010). The consequence of this difference is that it is much more difficult to perform chromosomal engineering in *Kluyveromyces* than in *S. cerevisiae*. During the evolution of *S. cerevisiae*, there was duplication of the whole genome (Dujon et al., 2004), which has had profound consequences for the genus, while such a duplication has not occurred during the evolution of the *Kluyveromyces* genus. Finally, there are fundamental physiological differences between *S. cerevisiae* on the one hand, and *K. lactis* and *K. marxianus* on the other hand. Deletion of the ScSDH1 gene (encoding a necessary subunit for succinate dehydrogenase) from *S. cerevisiae* blocks growth on lactate as the sole carbon source, whereas in *K. lactis*, deletion of the homologous gene does not affect growth on lactate (Saliola et al., 2004). Thus there are so many fundamental differences between *S. cerevisiae* and *K. marxianus* that the knowledge and teachings of the prior art for *S. cerevisiae* will not be sufficient to render it obvious how to best engineer non-*Saccharomyces* yeasts for production of succinate and other dicarboxylic acids without undue experimentation.

A combination of genetic engineering and metabolic evolution has been used to construct strains of *E. coli* that produce high levels of succinate (Zhang et al., 2009a; Zhang et al., 2009b; Jantama et al., 2008a; Jantama et al., 2008b). The process for metabolically evolving microbial organisms selected for organic acid production as described in the scientific references cited in the previous sentence is incorporated herein by reference.

Strains of *Saccharomyces cerevisiae, Kluyveromyces lactis, Issatchenkia orientalis, Candida* sp., *Torulopsis* sp., and *Zygosaccharomyces* have been disclosed that have been engineered to produce L-lactic acid and/or D-lactic acid (Zhang et al., 2011; U.S. Pat. Nos. 6,429,006, 7,049,108, 7,326,550, 7,229,805, and US Patent Application Publications 2009/0226989 and 2007/0031950).

Strains of *Saccharomyces cerevisiae* have been disclosed that have been engineered to produce L-malate (US Patent Application Publications 2008/0090273 and International Patent Application Publication WO 2009/011974). The idea for placing pyruvate carboxylase, malate dehydrogenase, and fumarase in the cytoplasm was also disclosed, as was a method for co-producing malate and succinate. Strains of *Issatchenkia orientalis* have been disclosed that have been engineered to produce malate or fumarate (WO 2012/

103263). However, this patent application does not disclose use of *Kluyveromyces* as a host for malate or fumarate production, nor does it disclose use of PEP carboxykinase for the carboxylation reaction from PEP to oxaloacetate (OAA).

Strains of *S. cerevisiae, Issatchnekia orientalis*, and *Yarrowia lipolytica* have been disclosed that have been engineered to overproduce succinic acid (WO 2008/128522, WO 2010/043197, US 2012/0040422, WO 2010/003728, WO 2011/023700, WO 2009/101180, WO 2012/103261, US 2012/0015415 and WO 2012/038390). Although several of the above listed applications claim to cover succinic acid production in any yeast, fungus or eukaryote, none the teachings of any of these publications comes close to enabling such broad claims. Furthermore, none of the published fermentation parameters in any of the above listed applications are economically attractive enough for commercial production. As such, there is still a need for, and ample room for, improvement over the current art for succinic acid production by fermentation at low pH.

SUMMARY OF THE INVENTION

The invention disclosed herein provides genetically engineered microorganisms that produce organic acids, such as succinic acid (succinate), malic acid (malate), D-lactic acid, L-lactic acid (lactate) and fumaric acid (fumarate) starting from renewable carbon sources, by fermentation at low pH. In a preferred embodiment, the microorganism is a derivative of a wild yeast strain that is more tolerant than *S. cerevisiae* strains to a desired organic acid at a low pH. In a more preferred embodiment, the wild strain is of the species *Kluyveromyces marxianus* or *Issatchenkia orientalis*, and the derivatives are genetically engineered.

In a preferred embodiment of the present invention, the genetically engineered organisms of the invention contain enzymes derived from at least a portion of the succinic acid biosynthetic pathway known from *E. coli* and *S. cerevisiae*, including a PEP carboxykinase. In another preferred embodiment of the present invention, at least a subset of the enzymes in the succinate biosynthetic pathways of the genetically engineered organisms of the invention are located in the cytoplasm (also known as the cytosol) instead of, or in addition to, being located inside the mitochondria. The combining of the oxidative and reductive pathways in one subcellular compartment allows for running the two pathways in a redox balanced manner. In yet another embodiment of the present invention, only the enzymes from the reductive TCA pathway are located in the cytoplasm, in which case the reducing equivalents are exchanged in and out of the mitochondria by well know shuttle systems, such as the glycerol-3-phosphate shuttle.

In a preferred aspect of the invention, the genetically engineered yeast cells of the invention will contain in the cytoplasm all enzymes necessary for both the oxidative and reductive pathways from phosphoenol pyruvate (PEP) to succinate, at sufficient levels to operate both the oxidative and reductive pathways in a balanced manner such that succinate is produced as the major fermentation product under anaerobic or microaerobic conditions. In one aspect of the present invention, one or more of the genes that encode said enzymes are derived from a yeast species. In another aspect of the invention, one or more of the genes that encode for a succinate pathway enzyme is derived from a bacterium and/or a yeast such as *S. cerevisiae* or *K. marxianus*. In yet another aspect of the present invention, the genes encoding all of the enzymes required for the oxidative and reductive pathways from PEP to succinate (including PEP carboxykinase, pyruvate kinase, pyruvate dehydrogenase, and all of the enzymes used in the oxidative and/or reductive branches of the TCA cycle) are derived from a bacterium. In another embodiment, the source of said genes is the bacterium *E. coli* and/or a yeast such as *S. cerevisiae* or *K. marxianus*.

In another embodiment of the present invention, the genetically engineered yeast producing succinic acid has an increased activity for FAD reductase. In one aspect of the present invention, the increased activity of FAD reductase is achieved by introducing one or more heterologous genes that code a FAD reductase.

In another embodiment of the present invention, genetically engineered yeast cell for the production of lactic acid is provided. In one aspect of the present invention, the genetically engineered yeast cells for the production of lactic acid comprises exogenous gene coding for lactate dehydrogenase gene. In yet another aspect of the present invention, the genetically engineered yeast cells for the production of lactic acid comprises modified version of exogenous glycerol dehydrogenase gene coding for a protein that catalyzes the formation of D-lactate from pyruvate.

In another embodiment of the present invention, genetically engineered yeast cells for the production of lactic acid, malic acid, fumaric acid and succinic acid are subjected to the process of metabolic evolution to increase the production of the respective acids further.

DETAILED DESCRIPTION OF THE PREFERRED EMBODIMENTS

Definitions

Figure 1:
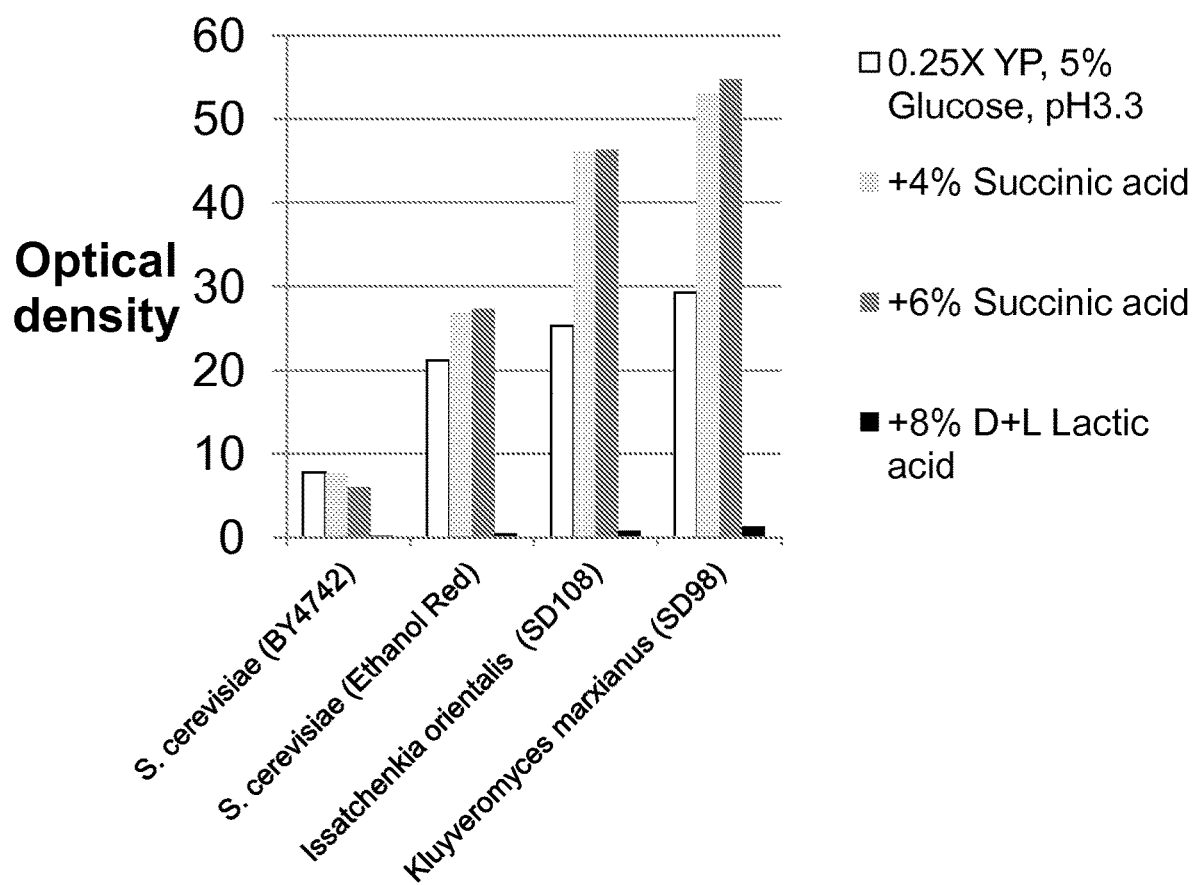
FIG. 1. Comparison of growth of yeast strains at low pH in the presence of organic acids in a rich growth medium. The yeast strains *Issatchenkia orientalis* (SD108) and *Kluyveromyces marxianus* (SD98) strains were isolated from rotting bagasse. *Saccharomyces cerevisiae* BY4742 is a standard laboratory strain and *Saccharomyces cerevisiae* Ethanol Red is a distillery strain.

As used in this patent application, the phrase "for example" or "such as" is meant to indicate that there are more than one method, approach, solution, or composition of matter for the subject at hand, and the example given is not meant to be limiting to that example.

Any carboxylic acid or dicarboxylic acid can be referred to by either using a free acid name, such as "succinic acid", or as a salt, ester, thioester, or amide, in which case the name could be referred to as "succinate". For example, the ammonium salt would be named ammonium succinate, and the ethyl ester would be ethyl succinate. Under physiological conditions in side of cells, and in fermentation broths outside of cells, the free acid and the salt will both be present to some extent, and the salt would have a mixture of counterions, so for the purposes of this invention, the two types of names shall both refer to both forms. In other phrases, "succinic acid" and "succinate" shall be used interchangeably and both shall refer to all forms of the compound. The same shall be true for all other organic acids.

For nomenclature, a gene or coding region from a bacterium such as E. coli is usually named with three lower case letters in italics, sometimes followed by an upper case letter, for example "mdh" or "fumB", for the genes encoding malate dehydrogenase or fumarase B, respectively, while the enzyme or protein encoded by a gene can be named with the same letters, but with the first letter in upper case and without italics, for example "Mdh" or "FumB", for malate dehydrogenase enzyme and fumarase B enzyme, respectively. A gene or coding region from a yeast such as S. cerevisiae or K. marxianus is usually named with three upper case letters, sometimes followed by an integer, all in italics, for example "PDC1", for a gene that encodes pyruvate decarboxylase, while the enzyme or protein encoded by a gene can be named with the same letters, but with the first letter in upper case and without italics, and followed by a lower case "p" for protein, for example "Pdc1p", for pyruvate decarboxylase 1. The enzyme or protein can also be referred to by the more descriptive name, for example, malate dehydrogenase, fumarase B, and pyruvate decarboxylase 1 for the examples given above. When referring to a gene or enzyme from a particular yeast species, a pair of letters abbreviating the first letter of the genus and species can be placed in front of the gene or enzyme to designate a particular version of the gene or enzyme. For example, ScMDH1 designates a malate dehydrogenase isozyme 1 from S. cerevisiae, while KmMDH1 designates a malate dehyhdrogenase 1 isozyme from K. marxianus. If no lower case letters are present to indicate a gene or enzyme from a particular species, for example "DIC1", then the gene name is meant to refer to the gene or enzyme form any and all yeast species. Note that these designations are not necessarily unique, in that any particular designation may not be limited to a particular DNA or protein sequence, since any given species can have many different strains, and different strains might have different genes or enzymes that perform the same function. In addition, a gene or coding region that encodes one example of an enzyme that posses a particular catalytic activity can have several different names because of historically different origins, or because the gene comes from different species.

A "plasmid" means a circular or linear DNA molecule that is substantially smaller than a chromosome, separate from the chromosome or chromosomes of a microorganism, and that replicates separately from the chromosome or chromosomes. A "plasmid" can be present in about one copy per cell or in more than one copy per cell.

An "expression cassette" means a DNA sequence that can be part of a chromosome or plasmid that contains at least a promoter and a gene or region that codes for an enzyme or other protein, such that the coding region is expressed by the promoter, and the enzyme or protein is produced by a host cell that contains the DNA sequence. An "expression cassette" can be at least partly synthetic, or constructed by genetic engineering methods, so that the coding region is expressed from a promoter that is not naturally associated with the coding region. Optionally, the "expression cassette" can contain a transcription terminator that may or may not be a terminator that is naturally associated with the coding region. An "expression cassette" can contain coding regions for more than one protein. In some cases the cassette will have only one promoter that is functionally coupled to the gene at the 5' end of the DNA sequence, in which case it can be called an operon, or a synthetic operon. In other cases, an expression cassette containing more than one coding region will have a different promoter functionally coupled to each coding region in the cassette, such that each coding region is expressed at an appropriate level in the host strain, such as a yeast strain.

"Overexpression" of a gene or coding region means causing the enzyme or protein encoded by that gene or coding region to be produced in a host microorganism at a level that is higher than the level found in the wild type version of the host microorganism under the same or similar growth conditions. This can be accomplished by, for example, one or more of the following methods: 1) installing a stronger promoter, 2) installing a stronger ribosome binding site, 3) installing a terminator or a stronger terminator, 4) improving the choice of codons at one or more sites in the coding region, 5) improving the mRNA stability, and 6) increasing the copy number of the gene, either by introducing multiple copies in the chromosome or placing the cassette on a multicopy plasmid. An enzyme or protein produced from a gene that is overexpressed is said to be "overproduced". A gene that is being "overexpressed" or a protein that is being "overproduced" can be one that is native to a host microorganism, or it can be one that has been transplanted by genetic engineering methods from a donor organism into a host microorganism, in which case the enzyme or protein and the gene or coding region that encodes the enzyme or protein is called "foreign" or "heterologous". Foreign or heterologous genes and proteins are by definition overexpressed and overproduced, since they are not present in the unengineered host organism.

A "homolog" of a first gene, DNA sequence, or protein is a second gene, DNA sequence, or protein that performs a similar biological function to that of said first gene, DNA sequence or protein, and that has at least 25% sequence identity (when comparing protein sequences or comparing a protein sequence derived from a gene sequence using the appropriate genetic code) with said first gene or protein, as determined by the BLAST computer program for sequence comparison (Saliola et al., 2004; Altschul et al., 1997; Altschul et al., 1990), and allowing for deletions and insertions. An example of a homolog of the *S. cerevisiae* gene ScURA3 would be the KmURA3 gene from *K. marxianus*.

An "analog" of a first gene, DNA sequence, or protein is a second gene, DNA sequence, or protein that performs a similar biological function to that of said first gene, DNA sequence, or protein, but where there is less than 25% sequence identity (when comparing protein sequences or comparing the amino acid sequence derived from gene sequences) with said first gene, DNA sequence or protein, as determined by the BLAST computer program for sequence comparison (Altschul et al., 1990; Altschul et al., 1997), and allowing for deletions and insertions. For example, KlFum1p, fumarase 1 from *K. lactis*, is an analog of FumB from *E. coli*, since they both function as fumarase, but there is no significant sequence homology between the two enzymes or their respective genes. A scientist knowledgeable in the art will know that many enzymes and proteins that have a particular biological function, for example fumarase or malate dehydrogenase, can be found in many different organisms, either as homologs or analogs, and since members of such families of enzymes or proteins share the same function, although they may be slightly or substantially different in structure, different members of the same family can in many cases be used to perform the same biological function using current methods of genetic engineering. Thus, for example, the KmFum1p fumarase from *K. marxianus* and the FumB fumarase from *E. coli* both catalyze the same reaction, so either one can result in production of fumaric acid and ultimately succinic acid in the proper context, and the choice of which one to use ultimately can be made by choosing the one that leads to a higher titer of fumaric or succinic acid under similar fermentation conditions.

A "strong constitutive promoter" is a DNA sequence that typically lies upstream (to the 5' side of a gene when depicted in the conventional 5' to 3' orientation), of a DNA sequence or a gene that is transcribed by an RNA polymerase, and that causes said DNA sequence or gene to be expressed by transcription by an RNA polymerase at a level that is easily detected directly or indirectly by any appropriate assay procedure. Examples of appropriate assay procedures include 1) quantitative reverse transcriptase plus PCR, 2) enzyme assay of an encoded enzyme, 3) Coomassie Blue-stained protein gel, or 4) measurable production of a metabolite that is produced indirectly as a result of said transcription, and such measurable transcription occurring regardless of the presence or absence of a protein that specifically regulates level of transcription, a metabolite, or inducer chemical. An example of a promoter that is not a "strong constitutive promoter" is the $P_{lac}$ promoter of *E. coli*, or the promoter in front of the KlLAC4 gene, since both genes are negatively regulated in the absence of an inducer such as lactose. By using well known methods in the art, a "strong constitutive promoter" can be used to replace a native promoter (a promoter that is otherwise naturally existing upstream from a DNA sequence or gene), resulting in an expression cassette that can be placed either in a plasmid or chromosome and that provides a level of expression of a desired DNA sequence or gene at a level that is higher than the level from the native promoter. A strong constitutive promoter can be specific for a species or genus, but often a strong constitutive promoter from a bacterium or yeast can function well in a distantly related bacterium or yeast, respectively. For example, a promoter from *S. cerevisiae* can function well in *K. lactis* or *K. marxianus* (Lee et al., 2012). Examples of strong constitutive promoters are promoters that drive expression of the genes that encode enzymes in the glycolytic pathway, genes that encode ribosomal proteins, and genes that encode translation elongation factors (Sun et al., 2012).

"The major fermentation product" means a product of fermentation other than water or carbon dioxide that is produced at a concentration that is higher than any other fermentation product.

The plasmids and gene cassettes disclosed herein can be constructed or obtained by any of a number of methods well known in the art, including cloning of DNA in plasmid libraries, restriction enzyme digestion and ligation, PCR amplification, recombineering in yeast, and the so-called Gibson method using a commercially available kit (for example New England Biolabs, Ipswitch, Mass., USA). Desired DNA sequences can also be custom synthesized by commercial companies that specialize in this service, such as GeneArt (Life Technologies, Carlsbad, Calif., USA) and DNA 2.0 (Menlo Park, Calif., USA).

The following examples are intended to be illustrative, but not limiting, and one skilled in the art will recognized that many variations are possible within the scope of this invention.

Example 1

Construction of Yeast Strains that Contain a Redox-Balanced Microaerobic Pathway from Glucose to Malate or Fumarate The reductive pathway from glucose to malate or fumarate is redox balanced, since glycolysis produces one mole of NADH per three carbon unit, and the malate dehydrogenase step consumes one mole of NADH. Thus, in the absence of other considerations, a cell should be able to produce malate or fumarate from glucose anaerobically. However, excess reducing equivalents from cell mass biosynthesis prevent this from being allowed under strictly anaerobic conditions (see below). Nonetheless, under well controlled microaerobic conditions (less than 0.1 volume of air per volume of liquid per minute), the excess NADH generated from cell mass can be oxidized to allow growth and production of malate and fumarate. To create engineered strains that produce malate or fumarate microaerobically, deletions are introduced in one or more genes that are necessary for fumarate reductase and succinate dehydrogenase, to prevent fumarate from being metabolized to succinate, either in the cytoplasm or in the mitochondria. In *Saccharomyces cerevisiae*, these genes are annotated as SDH1, SDH2, SDH3, and SDH4 for the four subunits that encode succinate dehydrogenase (Robinson and Lemire, 1996), and FRD1 and OSM1 for the genes that encode cytoplasmic and mitochondrial fumarate reductase, respectively. It is well documented that deletion of both FRD1 and OSM1 in a wild type background leads to lack of growth under anaerobic conditions, due to failure to reoxidize $FADH_2$ to FAD (Camarasa et al., 2007). However, microaerobic conditions will alleviate this growth problem.

After deletion of genes that encode enzymes that can catalyze decarboxylation of pyruvate (PDC) and conversion of fumarate to succinate, gene expression cassettes are introduced that confer production of cytoplasmic PEP carboxykinase, malate dehydrogenase, and, optionally, if fumarate is a desired product, fumarase. For example, pck, mdh, and fumB and/or fumC, all from *E. coli* can be used. In another aspect of this invention, genes from other bacteria can be used. In a preferred embodiment, fumC from *E. coli* is used, because the FumC enzyme does not require any iron-sulfur cluster, and iron sulfur clusters are made in the mitochondria in yeasts (Avalos et al., 2013), so it is preferable for a cytoplasmic enzyme to not depend on an iron-sulfur cluster. Alternatively, yeast genes can be used, such as MDH2 or modified MDH3 (Zelle et al., 2008) and modified FUM1 (Stein et al., 1994) from *S. cerevisiae*, or their homologs from *K. marxianus, I. orientalis*, or *H. polymorphs*. One skilled in the art will know that the difference between producing malate and fumarate will be the difference between not having a fumarase expressed in the cell, in which case malate will be produced, and having fumarase expressed in the cell, in which case, fumarate will be produced as well as at least some malate.

Installation of the expression cassettes can be accomplished by non-homolgous, or preferably homologous, integration into the chromosome, or by installation of a replicating plasmid that contains the desired cassette(s). Assembly of more than one gene, each with its own promoter and terminator, into a package that can be manipulated as one contiguous DNA sequence for either integration into a chromosome or into a replicating plasmid, is well known in the art (Shao et al., 2012).

After deleting the genes as described above and installing expression cassettes for the reductive pathway to malate or fumarate are completed in a single strain, the resulting engineered strain is subjected to metabolic evolution to select for more rapid growth. The metabolic evolution can be conducted in a chemically defined medium, such as yeast nitrogen base (YNB, available from Sigma Chemical Company, USA) supplemented with 100 g/l glucose and any other nutrients required by the strain. Microaerobic fermentors with pH control set at about between pH 2 and pH 5 are used to grow the strains to be evolved, and serial inoculations from fully grown fermentors to fresh fermentors are made repeatedly at appropriate intervals (usually from about one day to about 5 days of growth at a temperature of between about 20° C. and 50° C.) by adding one volume of inoculum to about 5 or more volumes of fresh medium. This process is repeated as necessary until an economically attractive growth rate is obtained. As acid is produced, the control of pH can be accomplished for example by addition of a carbonate salt, or a mixture of the hydroxide, carbonate and bicarbonate salts of ammonia, sodium, potassium, magnesium, or calcium.

Example 2

Construction of Yeast Strains that Contain a Redox-Balanced Anaerobic Pathway from Glucose to Succinate Anaerobic and microaerobic succinate biosynthesis from glucose is more complicated than for malate or fumarate, since the reductive pathway to succinate consumes more reducing equivalents than can be obtained from glycolysis. The best possible yield of succinate biosynthesis from glucose is obtained by running the oxidative and the reductive pathways in a ratio that results in no net production or consumption of redox equivalents, such redox equivalents usually being in the form of NADH, NADPH, and $FADH_2$, but also possible in the form of other compounds such as cysteine, glutathione, Coenzyme A-SH, and others. Taking into account only the pathways from glucose to succinate, this balance is theoretically obtained by having about 5 moles of glucose metabolized through the reductive pathway while simultaneously having about 2 moles of glucose metabolized through the oxidative pathway. It is difficult, if not impossible, to arrange for this precise balance by using materials and methods disclosed in the prior art. Moreover, in any fermentation process, including glucose to succinate, it is necessary to create cell mass, and the creation of cell mass under anaerobic conditions results in a net production of reducing equivalents. In wild type yeasts, such as *Saccharomyces, Kluveromyces, Candida*, and *Issatchenkia*, where ethanol and carbon dioxide are the major fermentations products, these excess reducing equivalents are disposed of by secreting glycerol. However, secretion of glycerol costs carbon that could otherwise be used for succinate, malate or fumarate. As such, if the ratio of reductive to oxidative pathway is slightly higher than 5:2 (with respect to moles of glucose metabolized through each pathway), then redox balance for the entire cell, including succinate production and cell mass production, can be achieved. However, once again, this balance is difficult or impossible to achieve by materials and methods disclosed in the prior art.

The present inventors have recognized the subtleties disclosed above, and have provided herein materials and methods to solve the problems.

The first step in engineering a yeast for succinate production from glucose is to create a host strain where the unwanted fermentative pathways have been reduced in flux or deleted. In yeasts of the genera *Saccharomyces, Kluyveromyces, Candida, Pichia, Hansenula* and *Issatchenkia*, the predominant fermentative pathways are to ethanol (plus carbon dioxide) and glycerol. Flux to ethanol can be decreased or blocked by deleting all genes encoding pyruvate decarboxylase (EC 4.1.1.1). *Saccharomyces cerevisiae* has three such genes, ScPDC1, ScPDC5, and ScPDC6. *Kluyveromyces lactis* and *K. marxianus* each have only one pyruvate decarboxylase gene, KlPDC1 and KmPDC1, respectively. Flux to glycerol can be decreased or blocked by deleting all genes encoding glycerol-3-phosphate dehydrogenase (EC 1.1.1.8; EC 1.1.99.5; EC1.1.1.177; EC 1.1.1.94). *S. cerevisiae* contains three such genes, GUT2, GPD1, and GPD2. *K. lactis* contains two such genes, KlGUT2 (Saliola et al., 2008) and KlGPD1 (Neves et al., 2004). *K. marxianus* contains genes homologous to the *K. lactis* genes, and that perform the same function. If the glycerol biosynthetic pathway is blocked in this fashion, then the cell's requirement for glycerol can be met by feeding a relatively small amount of glycerol. Alternatively, the flux to glycerol can be decreased or blocked by deleting all genes encoding glycerol-3-phosphate phosphatase (EC 3.1.3.21). *S. cerevisiae, K. lactis*, and *K. marxianus* each contain a gene named GPP1, or a homolog thereof, and which can be deleted for the purpose of reducing or eliminating flux to glycerol.

In a preferred embodiment, the genes that encode all of the enzymes necessary for both the reductive pathway and the oxidative pathway from glucose to succinate are cloned and installed such that they are all expressed from strong constitutive promoters. In another preferred embodiment, all of the necessary enzymes for both the reductive and oxidative pathways are directed to the cytoplasm. The enzymes necessary for the reductive pathway include PEP carboxykinase (EC 4.1.1.49), malate dehydrogenase (EC 1.1.1.37), fumarase (EC 4.2.1.2), and fumarate reductase (EC 1.3.1.6). The enzymes necessary for the oxidative pathway include pyruvate kinase (EC 2.7.1.40), pyruvate dehydrogenase (EC 1.2.4.1), citrate synthase (EC 4.3.1.7 or 4.3.1.28), aconitase (EC 4.2.1.3), isocitrate dehydrogenase (EC 2.7.1.40), α-ketoglutarate dehydrogenase, (EC 1.2.4.2) and succinyl-CoA synthetase, also known as succinate-CoA ligase (EC 6.2.1.4 or EC 6.2.1.5). Some of these enzymes require more than one subunit to function, in which case, genes encoding all subunits need to be cloned and expressed.

The cloning of the necessary genes can be achieved by any of a number of methods well known in the art, for example gene library construction in an appropriate plasmid, cosmid, phagemid, bacterial artificial chromosome, or yeast artificial chromosome, followed by screening using a DNA probe or selection by functional complementation in an appropriate mutant host cell, for example a bacterium or yeast strain. The DNA sequence for many such genes have been published and are available on the National Center for Biotechnology Information website, http://www.ncbi.nlm.nih.gov/pubmed/, for example, from *E. coli*, *S. cereveisae*, and *Kluyveromyces lactis*. For these cases, the desired gene can be amplified and cloned by polymerase chain reaction (PCR) and then cloned in an appropriate vector. To obtain the DNA sequence for a desired gene from an organism, or for which the DNA sequence has not yet been published, for example from *Issatchenkia orientalis* or *Kluyveromyces marxianus*, one can obtain the DNA sequence for the entire genome by well established methods and locate the desired gene by homology to a known gene from another organism (Altschul et al., 1997; Altschul et al., 1990). Then the desired gene can be amplified by PCR and cloned in an appropriate expression vector or expression cassette.

After each desired gene is cloned, any sequence that would direct the native (wild type) protein to a subcellular organelle other than the cytoplasm is deleted or mutated so as to substantially prevent the protein from being imported into said organelle. Methods for accomplishing this are well known in the literature. For example, it is known that the N-terminal protein sequence of a protein targeted to the mitochondrial matrix (the inner chamber of the mitochondria) can be deleted to redirect the protein to the cytoplasm. "The N-terminal targeting sequences" are also called matrix targeting sequences (MTSs) because they also bring the N terminus across the inner membrane into the matrix. In the absence of further sorting information, they direct proteins into the matrix. They have been studied in considerable detail, and their main characteristics have been known for more than 10 years. They consist of about 10-80 amino acid residues that have the potential to form amphipathic helices with one hydrophobic and one positively charged face. There is no consensus in the primary structure, which often differs considerably even between closely related orthologs. However, the general properties of these amphipathic helices are "widely conserved among fungi and animals" (Neuport and Hermann, 2007). One specific example is that the wild type fumarase encoded by the ScFUM1 gene is directed to both the mitochondria and the cytoplasm, but if the DNA sequences encoding the N-terminal 17 amino acids are deleted, then none of the enzyme is found in the mitochondria (Stein et al., 1994). An example of redirecting a peroxysomal malate dehydrogenase to the cytoplasm was accomplished by deleting the 9 base pairs encoding the C-terminal tripeptide sequence, SKL, from the MDH3 gene (Zelle et al., 2008).

After any organelle targeting sequence has been deleted or mutated, the gene for each desired enzyme is functionally coupled to a constitutive promoter. In a preferred embodiment, each of the desired genes is coupled to a different promoter, so that the gene expression cassettes can be assembled together in one array without having any substantially repeated DNA sequences in the array, which in turn makes it more convenient to integrate the assembled array into a chromosome of the intended host strain or into a plasmid as a vehicle for introducing the assemble array.

After the array is assembled, it is installed in the host strain described above. A specific example of redirecting what is normally a mitochondrial enzyme to the cytoplasm is given in Example 11.

Installation of the expression cassettes can be accomplished by non-homolgous, or preferably homologous, integration into the chromosome, or by installation of a replicating plasmid that contains the desired cassette(s). Optionally, installation of an expression cassette can be combined with deletion of one or more of the unwanted genes, for example KmPDC1, such that the cassette substitutes for the unwanted gene, in effect accomplishing two of the desired steps at once. The promoter of the unwanted gene can be arranged to be used to drive expression of one of the desired genes. For example, integration of a cassette designed to give expression of the *E. coli* pck gene at the KmPDC1 locus can be designed so that the pck open reading frame precisely replaces the KmPDC1 open reading fame. If more than one gene are to be expressed from the cassette, then it can be arranged so that the last gene of the array is functionally coupled to the KmPDC1 terminator.

After deleting the genes as described above and installing expression cassettes for the reductive, and preferably the oxidative, pathways to succinate is completed in a single strain, the resulting engineered strain is subjected to metabolic evolution to select for more rapid growth. The metabolic evolution can be conducted in a chemically defined medium, such as yeast nitrogen base (YNB) supplemented with 100 g/l glucose and any other nutrients required by the strain. Microaerobic fermentors with pH control set at about between pH 2 and pH 5.6 are used to grow the strains to be evolved, and inoculation from a fully grown fermentor to a fresh fermentor is made by adding one volume of inoculum to about 5 or more volumes of fresh medium. Spontaneous mutations occur in the population, and any mutant that grows more rapidly than its parent will take over the population. This process is repeated as necessary until an economically attractive growth rate is obtained by this evolutionary process. As acid is produced, the control of pH can be accomplished for example by addition of a carbonate salt, or a mixture of the hydroxide, carbonate and bicarbonate salts of ammonia, sodium, potassium, magnesium, or calcium.

Example 3

Isolation of Wild Yeast Strains

Wild yeast strains were isolated by enriching for their growth from a rotting sugarcane bagasse sample in ¼ strength YP medium (2.5 g/l yeast extract plus 54 g/l peptone), pH 5 containing 5% xylose and antibiotics (chloramphenicol, 30 mg/l, and ampicillin, 150 mg/l) in shake flasks fitted with bubblers (gas traps; available from the Homebrew Emporium, Cambridge, Mass., USA) and incubated with gentle shaking at 30° C. for 48 hrs. Thus the resulting isolates were selected to utilize xylose anaerobically or at least microaerobically, if not strictly anaerobically, and be able to grow at low pH, since the medium is unbuffered and the pH decreases naturally during growth of the culture. The enriched cultures were then plated on either YP plus 2% xylose plates with chloramphenicol and ampicillin or on minimal (Difco Yeast Nitrogen Base, or "YNB") medium with 2% Xylose and chloramphenicol and ampicillin and incubated aerobically at 30° C. Yeast colonies were purified on the same plates and then the species were identified by sequencing of a region of the D1/D2 domain of the large subunit of rDNA. Wild yeasts can be isolated from other niches such as fermentation facilities, fermented foods, contaminated foods, soil, plants, lakes, rivers, oceans, etc.

An alternative approach for isolating wild yeasts would be similar to that described in the above paragraph, but with the addition of an organic acid, such as succinic acid to the medium at about 5 to 60 g/l, and adjusting the pH to about 2.5 to 5.6. In this fashion, yeasts that are particularly tolerant to low organic acids at low pH can be directly selected for or enriched from samples. Moreover, the carbon source in the enrichment medium can be other than xylose, for example it could be glucose, sucrose, arabinose, starch, methanol or glycerol.

Example 4

Identification of Wild Yeast Strains by Sequencing the Genes Encoding Ribosomal RNA The D1/D2 domain of the large subunit of rDNA was amplified from the genomic DNA of the yeast species to be identified. The yeast species were obtained from rotting bagasse. The primers used for PCR and sequencing are listed below in Table 1.

PCR product from SD98 template DNA obtained with primers SD123 and 124 was sequenced with primers SD123, 124, 125, 126, 129, and 130 (Table 1). PCR product obtained with primers SD127 and 128 was sequenced with primers SD127 and 128. All 8 sequences were combined to obtain a 1725 bp long contiguous DNA sequence, which was found to be 100% identical with a *Kluyveromyces marxianus* strain CHY1612 18S ribosomal RNA gene, partial sequence (Genbank ID: HQ396523.1)

Yeast strain SD108 genomic DNA was used as template to generate a PCR product with primers SD123 and SD124. When sequenced with primers SD124 and SD125 this PCR product gave a 599 bp contiguous sequence which showed 100% identity with *Issatchenkia orientalis* (also known as *Pichia kudriavzevii*) strain NRRL Y-5396 rDNA (Genbank ID EF550222.1).

Example 5

Yeast from the Species *Kluyveromyces marxianus* and *Issatchenkia Orientalis* are More Tolerant to Succinic Acid at Low pH than *S. cerevisiae*

Newly isolated yeast strains *Kluyveromyces marxianus* (SD98) and *Issatchenkia orientalis* (SD108) were compared with a standard laboratory strain of *Saccharomyces cerevisiae* (BY4742) and an industrially used distillery strain of *Saccharomyces cerevisiae* (Ethanol Red) for aerobic growth at 30° C. and pH 3.3.

Figure 2:
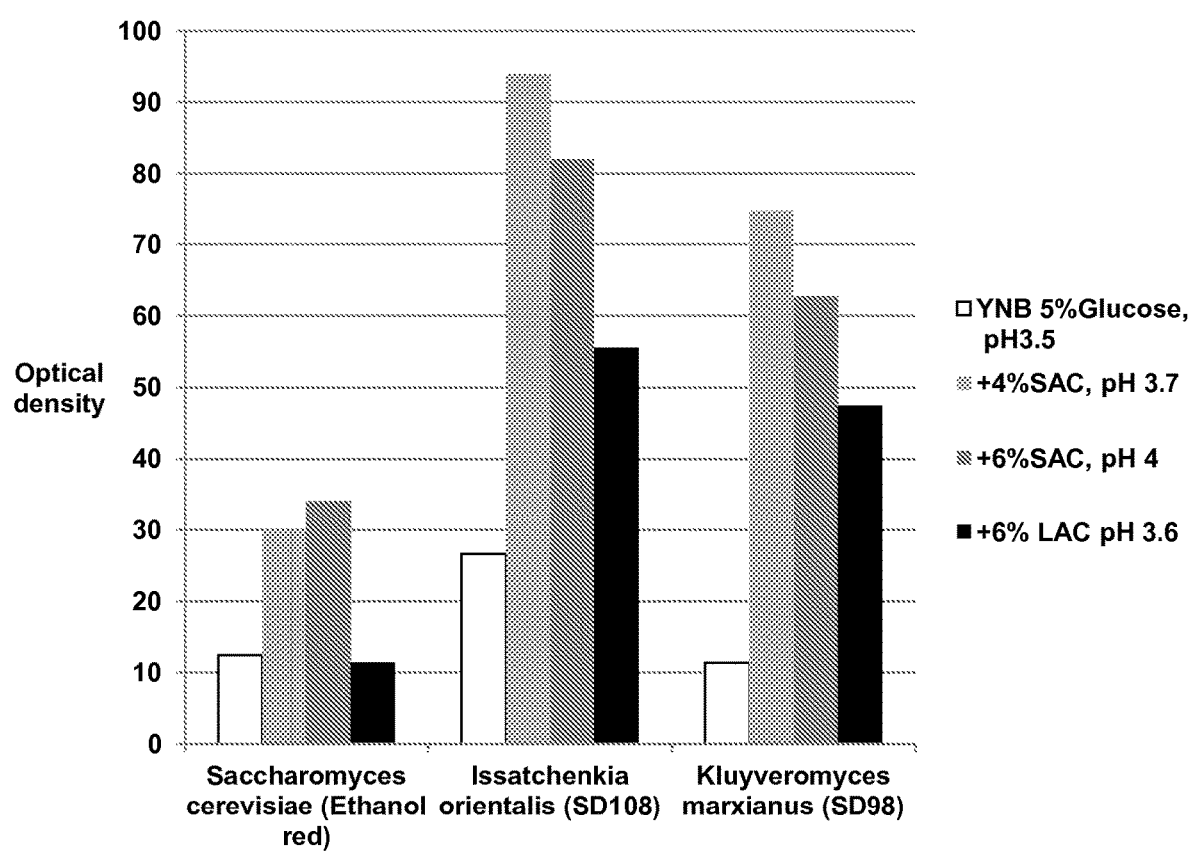
FIG. 2. Comparison of growth of yeast strains at low pH in the presence of organic acids in a minimal growth medium containing yeast nitrogen base. The yeast strains *Issatchenkia orientalis* (SD108) and *Kluyveromyces marxianus* (SD98) strains were isolated from rotting bagasse. *Saccharomyces cerevisiae* BY4742 is a standard laboratory strain and *Saccharomyces cerevisiae* Ethanol Red is a distillery strain.

All four yeast strains were inoculated from YP plus 2% glucose plates into liquid YP medium with 2% Glucose, pH 5, and incubated overnight at 30° C. aerobically. Overnight $OD_{600}$ was read and these cultures were used to inoculate 3 ml each of 0.25×YP with various organic acids. The final pH was 3.3, and the starting $OD_{600}$ was 0.1. The cultures were incubated at 30° C. aerobically for 46 hrs. $OD_{600}$ was read at 46 hrs. The final pH of cultures was also read and the pH of all four cultures were found to be around 3 (FIG. 1). Similar results were obtained in a chemically defined mineral medium (FIG. 2).

Example 6

Production of Succinic Acid in a Genetically Engineered Strain of *K. marxianus*

The following genes from either *Escherichia coli* or *Saccharomyces cerevisiae* are integrated together as a cassette replacing the exact open reading frame of the pyruvate decarboxylase (PDC1) gene on the chromosome of *Kluyveromyces marxianus* (SD98): pck (coding for pyruvate carboxykinase) from *Escherichia coli*; mdh (coding for malate dehydrogenase) from *Escherichia coli*; fumB or fumC (coding for fumarase) from *Escherichia coli*; FRD1 (coding for fumarate reductase from *Saccharomyces cerevisiae*). A kanMX marker coding for G418 resistance (Wach et al., 1994) is also part of the integrating cassette.

The above mentioned genes are each flanked by a promoter and terminator sequence from *Kluyveromyces marxianus* (Km) or *Saccharomyces cerevisiae* (Sc) and representative examples of suitable promoter and terminator sequences are indicated below in the Table 2.

The cassette described above provides all the enzymes required for conversion of PEP to succinic acid via the reductive arm of TCA cycle. All these enzymes are expressed in the cytoplasm (cytosol) of the yeast cell. The cassette is designed to integrate at the KmPDC1 locus such that the first gene in the cassette, pck, is transcribed from the KmPDC1 promoter.

To further improve the efficiency of conversion to succinic acid, expression of each of the above genes is further optimized by changing the DNA sequences in accordance with the codon bias of *Kluyveromyces marxianus*.

The example provided above can also be applied to other acid tolerant yeast strains, such as SD108 strain of *Issatchenkia orientalis*.

Example 7

Providing $FADH_2$ for the Fumarate Reductase Reaction

The last step in the reductive pathway to succinate in both *E. coli* and yeast is catalyzed by fumarate reductase, with $FADH_2$ as the cofactor that supplies the reducing equivalent. As mentioned above, in order for a cell to produce succinate anaerobically or microaerobilcally, the cell must combine both a reductive and an oxidative pathway. The reductive pathway consumes reducing equivalents as NADH at the malate dehydrogenase step and $FADH_2$ at the fumarate reductase step, while the oxidative pathway produces reducing equivalents as NADH and NADPH. In order for redox balance to be achieved using the native fumarate reductase, the cell must be able to transfer reducing equivalents from NADH and NADPH to FAD. KJ122, an *E. coli* strain developed for succinate production (Jantama et al., 2008a; Jantama et al., 2008b) contains at least three genes that encode enzymes that can perform this function. The hpaC gene is present in *E. coli* C, *E. coli* W, and *E. coli* B (Galan et al., 2008; Roper et al., 1993), and the fre gene (also known as ubiB) is present in most or all strains of *E. coli* (Louie et al., 2002; Louie et al., 2003; Niviere et al., 1999). Both these genes encode an NAD(P)H-flavin oxidoreductase (also known as FAD:NADH reductase, FAD:NADPH reductase, or simply FAD reductase) that functions to recharge FAD to $FADH_2$ with reducing equivalents donated from NADH or NADPH. Yet another enzyme that is known to carry out this function is the alpha subunit of *E. coli* sulfite reductase, encoded by cysJ, which is known to use NADPH as a substrate for reduction of FAD (Coves et al., 1993; Eschenbrenner et al., 1995). However, yeast is not known to contain such an enzyme (Camarasa et al., 2007). As such, the important function of FAD reductase needs to be supplied by installing and expressing (as described elsewhere herein for other heterlogous genes) an hpaC gene, or a fre gene, or a homologous or analogous gene with similar function, in a yeast strain engineered to produce succinate. Equivalent genes include, but are not limited to, the prnF gene from *Pseudomonas fluorescens* (Tiwari et al., 2012), the hpaC gene from *E. coli* W (Galan et al., 2008; Roper et al., 1993), the fre gene from *E. coli* (Louie et al., 2002; Louie et al., 2003; Niviere et al., 1999), or the cysJ gene of *E. coli* (Coves et al., 1993; Eschenbrenner et al., 1995). This principle of providing FAD reductase to allow redox balance during anaerobic succinate production is widely applicable, not only to yeast, but to any other microbe engineered for high level succinate production. The source of such genes can also vary widely, the only requirement being that the gene provides adequate FAD reductase activity in the microbe engineered for succinate production. In the case where the FAD:NADH reductase cannot adequately use NADPH as the donor of reducing equivalents, it could be necessary to also install and express one or more genes that encode a transhydrogenase (such as the membrane bound enzyme (EC 1.6.1.2) encoded by pntA plus pntB genes of *E. coli*, or the sth gene (also known as udhA) that encodes a soluble transhydrogenase (EC 1.6.1.1) (Cao et al., 2011; Nissen et al., 2001; Anderlund et al., 1999).

Example 8

Production of D-Lactate by Acid Tolerant Yeast

A glycerol dehydrogenase from *Bacillus coagulans* has been recently shown to have the capability of being evolved to have a novel activity of producing D-lactate from pyruvate (Wang et al., 2011). The gene that encodes glycerol dehydrogenase (EC 1.1.1.6) in *B. coagulans* is named gldA, and the evolved form is named gldA101. A yeast can be converted from an ethanol producer to a D-lactate producer by deleting one or more genes that function in ethanol production (for example ScPDC1, SCPDC5, and ScPDC6, or KmPDC1, or IoPDC1) and installing an expression cassette that expresses the gldA101 gene or a homolog or analog thereof. The resulting yeast strain can then be subjected to metabolic evolution as described above to increase growth and productivity of D-lactate. Many genes that are homologous to gldA of *B. coagulans* can be found in public databases using a BLAST search with the default parameters (Altschul et al., 1990; Altshcul et al., 1997) and evolved as described (Wang et al., 2011). Yeast strains that are particularly tolerant to low pH, such as those described herein, are preferred host strains for producing D-lactate using this approach.

Example 9

Production of D-Lactate by Acid Tolerant Yeast

As an alternative to Example 9, a yeast can be converted from an ethanol producer to a D-lactate producer by deleting one or more genes that function in ethanol production (for example ScPDC1, SCPDC5, and ScPDC6, or KmPDC1, or IoPDC1) and installing an expression cassette that expresses the ldhA gene of *E. coli*, or a homolog or analog thereof, which encodes a D-lactate dehydrogenase (an enzyme that catalyzes the conversion of pyruvate plus NADH into D-lactate plus NAD; EC 1.1.128). The resulting yeast strain can then be subjected to metabolic evolution as described above to increase growth, rate of production, and tolerance to high concentrations of D-lactate. Many genes that are homologous to ldhA of *E. coli* can be found in public databases using a BLAST search with the default parameters (Altschul et al., 1990; Altshcul et al., 1997) and evolved as described (Jantama et al., 2008). Yeast strains that are particularly tolerant to low pH, such as those described herein, are preferred host strains for producing D-lactate using this approach.

In one example, the open reading frame from the PDC1 gene of *K. marxianus* strain SD98 was precisely replaced in the chromosome by the open reading frame from the ldhA gene of *E. coli* C, and the PDC1 terminator was left in place. Downstream from the terminator, a kanMX cassette (Wach et al., 1994) was installed, followed by a DNA sequence that naturally exists just downstream of the PCD1 terminator to provide homology for homologous recombination into the *K. marxianus* chromosome. The plasmid that was built containing this cassette was named pSD57 (SEQ ID No. 1). A linear DNA fragment was produced from this plasmid by PCR using primers SD336 and SD343, and used to transform SD98 using selection with 200 mg/L antibiotic G418 (also known as Geneticin), to give novel strain isolates. The correct desired gene replacement was confirmed in a subset of the isolates by diagnostic PCR using the same primers. After restreaking several isolates on plates containing antibiotic G418, an isolate was obtained that produced D-lactate, but no ethanol. This homozygous diploid isolate, confirmed by diagnostic PCR, was named SD517.

SD517 was grown in a small scale (200 ml) microaerobic fermentor at 37 degrees C., using a defined medium (Difco Yeast Nitrogen Base) containing 100 g/L glucose, and supplemented with 10 microgram/L biotin, 1 mg/L niacin, and 1 mg/L thiamine hydrochloride, and stirring at 270 RPM. pH was set at 5.0 and controlled by addition of 2 M KOH as needed. 15 g/l D-lactate was produced in 192 hours.

A single colony was isolated from the fermentor at 192 hours, and named SD517-1-2. This new strain produced 30 g/l D-lactate in 192 hours in a similar fermentation, indicating that the strain had evolved for faster growth, better D-lactate production, and or better tolerance to D-lactate. A single colony isolated form the end of this fermentation was named SD517-D1.

The process described in the above paragraph was repeated again, with the new colony-isolated strain named SD517-D1, with the additional change that ergosterol (20 mg/L final concentration) and Tween 80 (final concentration 0.05%) were added to the medium. SD517-D1 produced 38 g/L D-lactate in 168 hours. The pH was controlled with 2 M KOH, with a final set point of pH 3.5 The actual final pH was 3.9. Again, the higher titer indicated that additional evolution may have taken place, and again, a single colony was saved from the end of the fermentation and named SD541.

Figure 3:
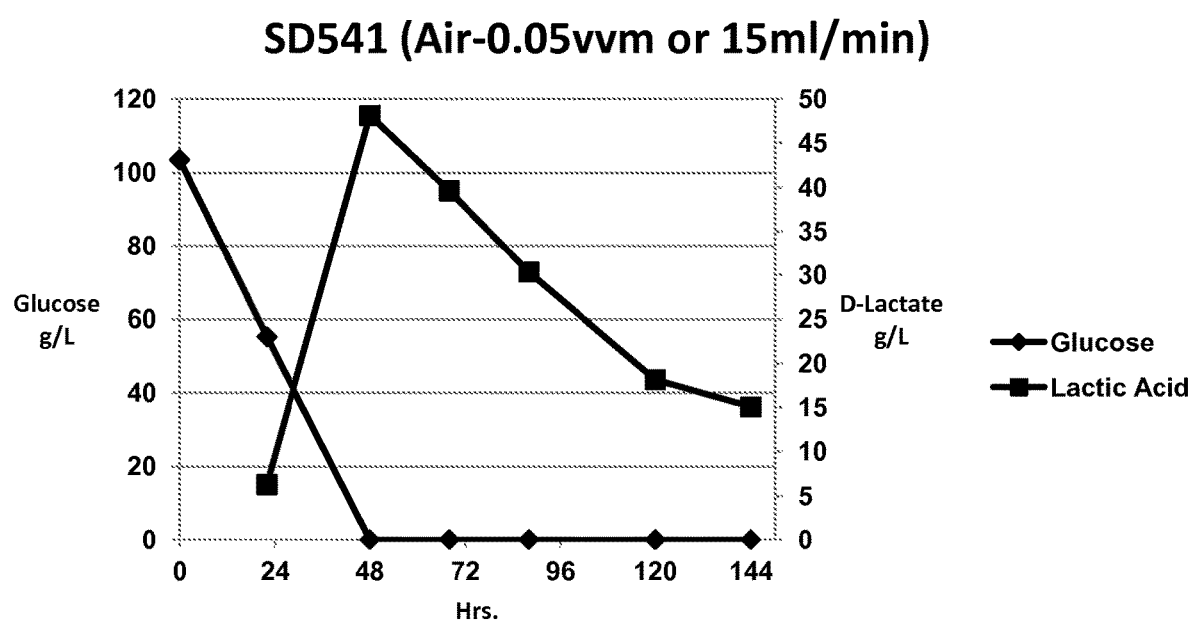
FIG. 3. Fermentative production of lactic acid by *Kluyveromyces marxianus* strain SD541 under microaerobic condition. *Kluyveromyces marxianus* SD98 strain was transformed with a plasmid carrying *E. coli* lactate dehydrogenase gene ldh to obtain strain SD517 which was subjected to metabolic evolution to obtain strain SD541.

The fermentation process described in the above paragraph was repeated, except that air was supplied at 15 ml/minute (0.05 volume/volume/minute or VVM). At 48 hours, 49 g/l D-lactate had been produced (see FIG. 3.), and the pH had fallen to 3.8. A single colony was isolated from the fermentor at 48 hours and named SD542. Again, the higher titer indicated that additional evolution may have taken place.

Example 10

Production of Succinate by Acid Tolerant Yeast

Figure 4:
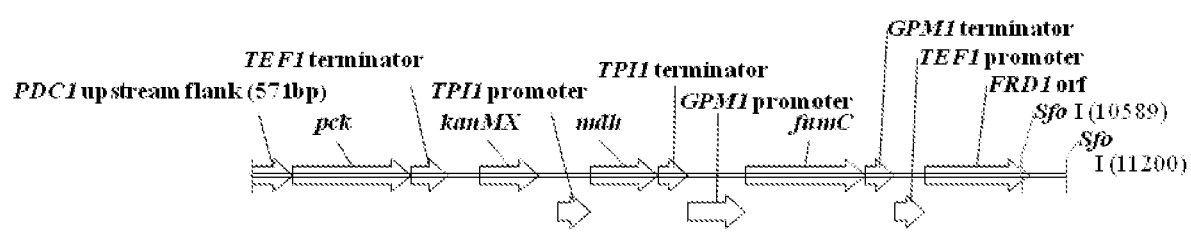
FIG. 4. Structure of a gene cassette with the genes coding for enzymes involved in the reductive pathway from phosphoenol pyruvate to succinate. This gene cassette codes for the enzymes PEP carboxykinase, malate dehydrogenase, fumarase, and fumarate reductase. The genes, the promoters, and the terminators used are listed in Table 2. A kanMX cassette was built into the middle of the cassette between pck and mdh genes.

A gene cassette was constructed to encode production of four enzymes sufficient to provide the reductive TCA pathway from PEP (phosphoenol pyruvate) to succinate, namely PEP carboxykinase (EC 4.1.1.49), malate dehydrogenase (EC 1.1.1.37), fumarase (EC 4.2.1.2), and fumarate reductase (EC 1.3.1.6). The genes, the promoters, and the terminators used are listed in Table 2. A kanMX cassette was built into the middle of the cassette between two of the genes. The structure of the cassette is shown in FIG. 4. The cassette was built into a plasmid named pSD59fumC (SEQ ID No. 2). A linear DNA fragment was produced from this plasmid as template by PCR using the primers SD390 and SD392. The linear DNA fragment was transformed into strain SD98, selecting for antibiotic G418 resistance at 200 mg/L. After restreaking transformed isolates on plates containing G418, a homozygous diploid isolate that contained the succinate biosynthetic cassette correctly integrated at the PDC1 locus in both homologous chromosomes was identified by diagnostic PCR and named SD631. A homozygous diploid control strain that contained only the kanMX cassette, which encodes resistance to antibiotic G418, at the PDC1 locus was also constructed and named SD565. SD565 did not contain the engineered succinate gene cassette.

Figure 5:
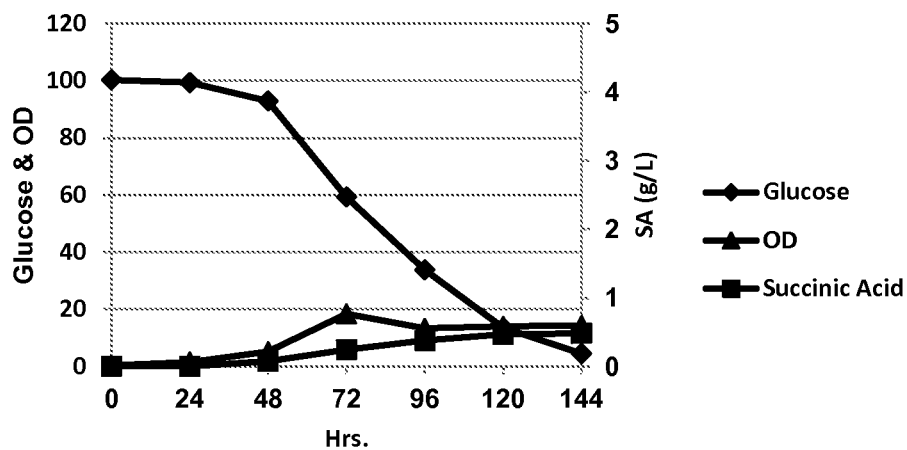
FIG. 5. Fermentative production of succinic acid in *Kluyveromyces marxianus* strain SD565 and *Kluyveromyces marxianus* strain SD631. SD565 has a G418 resistance marker cassette inserted at the pyruvate decarboxylase locus. SD631 has a G418 resistance marker cassette inserted at the pyruvate decarboxylase locus along with four other genes coding for the enzymes involved in the reductive pathway from phosphoenol pyruvate to succinate.
Figure 5:
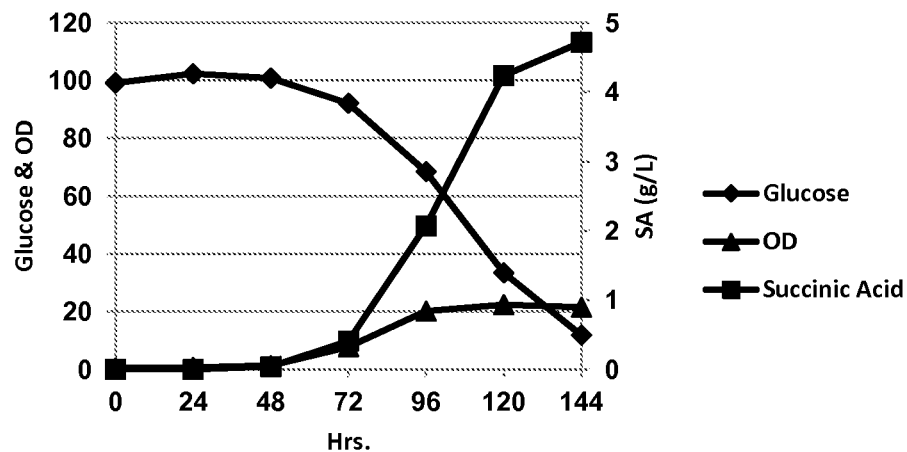

Both SD565 and SD631 were grown microaerobically in 200 ml fermentors at 37 degrees C. with a defined medium (Difco Yeast Nitrogen Base) containing 100 g/L glucose, and supplemented with 10 microgram/L biotin, 1 mg/L niacin, and 1 mg/L thiamine hydrochloride, The pH was allowed to fall to pH 5.0 and then maintained at pH 5.0 with 2 M ammonium bicarbonate. Air was supplied at 15 ml/minute and carbon dioxide was supplied at 6 ml/minute. Stirring was maintained at 270 RPM. In 144 hours, SD631 produced 4.7 g/L succinate, while SD565 produced only 0.5 g/L, indicating that the gene cassette in SD631 was functioning as designed (see FIG. 5.).

Strain SD631 can be further engineered to contain in the cytoplasm all enzymes necessary for both the oxidative and reductive branches of the TCA cycle as described below in Example, 11. Strain SD631 and derivatives thereof can be evolved to produce higher succinate titers, production rates, and tolerance to succinate by transferring inocula in successive small fermentors as described for *E. coli* succinate producers (Jantama et al., 2008). The pH set points can be lowered during the evolution to select for strains capable of producing and accumulating succinate at low pH.

Example 11

Redirection of a Mitochondrial Enzyme to the Cytoplasm

In yeasts, enzymes that are naturally found in the mitochondria are directed to the mitochondria by a signal sequence on the N-terminal end of the cytoplasmically translated polypeptide (Vogtle et al., 2009). Deletion of this signal sequence by deleting the DNA encoding the signal sequence results in a cytoplasmic location for the enzyme (Hurt et al., 1987). By generalization, it is well known in the art that any given enzyme that is naturally directed from the cytoplasm to the mitochondria can be engineered to be left in the cytoplasm by deleting the signal sequence. One specific example will be given here. The amino terminal sequence of the initial translation product of the IDH1 gene, which encodes mitochondrial isocitrate dehydrogenase (one of the enzymes of the oxidative branch of the TCA cycle), is MLNRTIAKRTLATAAQAER. The amino terminal sequence of the corresponding mature isocitrate dehydrogenase in the mitochondria is LATAAQAER. Thus, deletion of the DNA sequence CTTAACAGAACAATTGCTAAGAGAACT, will result in a shortened polypeptide with the initial translation product starting with an amino terminus of MLATAAQER . . . , which will remain in the cytoplasm because it lacks the mitochondrial signal sequence. By generalization of this method, any of the enzymes of the reductive or oxidate branches of the TCA cycle can be redirected to the cytoplasm. The mitochondrial enzymes necessary for the oxidative pathway include pyruvate dehydrogenase (EC 1.2.4.1), citrate synthase (EC 4.3.1.7 or 4.3.1.28), aconitase (EC 4.2.1.3), isocitrate dehydrogenase (EC 2.7.1.40), α-ketoglutarate dehydrogenase, (EC 1.2.4.2) and succinyl-CoA synthetase, also known as succinate-CoA ligase (EC 6.2.1.4 or EC 6.2.1.5). Some of these enzymes require more than one subunit to function, in which case, genes encoding all subunits need to be cloned and expressed. Genes encoding these enzymes and subunits include, but are not limited to, ScPDA1, ScPDB1, ScPDX1, ScLPD1, ScCIT1, ScCIT2, ScACO1, ScIDH1, ScKGD1, ScKGD2, ScLSC1, ScLSC2, and the related homologs and analogs from other yeasts such as *K. marxianus, K. lactis, Issatchenkia orientalis, Pichia pastoris,* and *Hansenula polymorphs.*

An alternative approach is to utilize genes and enzymes from bacteria such as *E. coli*, ruminant bacteria (*Actinobacillus, Mannheimia, Basfia,* among others), or other bacteria. Since bacteria do not have mitochondria, the heterologous enzymes and subunits thereof will be expressed and remain in the cytoplasm in yeast. In case a required enzyme is naturally encoded in the yeast mitochondrial genome, the preferred approach is to use a bacterial gene and enzyme for that case, since a mitochondrial signal sequence would not be present in the native protein, so redirecting it to the cytoplasm could be more difficult.

The invention disclosed herein can be practiced in any suitable yeast strain that has the property of being more tolerant than *Saccharomyces cerevisiae* to an organic acid at low pH. For example, *Candida magnolia* would be a suitable host strain (Zhang et al., 2011)

REFERENCES

U.S. Pat. No. 6,429,006
U.S. Pat. No. 6,485,947
U.S. Pat. No. 7,049,108
U.S. Pat. No. 7,141,410
U.S. Pat. No. 7,229,805
U.S. Pat. No. 7,326,550
U.S. Pat. No. 7,473,540
U.S. Pat. No. 7,534,597
U.S. Pat. No. 8,071,357
U.S. Pat. No. 8,137,953
U.S. Patent Application Publication No. US 2007/0031950
U.S. Patent Application Publication No. US 2008/0090273
U.S. Patent Application Publication No. US 2009/0226989
U.S. Patent Application Publication No. US 2010/0104771
U.S. Patent Application Publication No. US 2012/0015415
U.S. Patent Application Publication No. US 2012/0040422
International Patent Application Publication No. WO 2008/128522
International Patent Application Publication No. WO 2009/011974

International Patent Application Publication No. WO 2009/013159

International Patent Application Publication No. WO 2009/065777

International Patent Application Publication No. WO 2009/065778

International Patent Application Publication No. WO 2009/065779

International Patent Application Publication No. WO 2009/065780

International Patent Application Publication No. WO 2009/101180

International Patent Application Publication No. WO 2010/003728

International Patent Application Publication No. WO 2010/118932

International Patent Application Publication No. WO 2010/043197

International Patent Application Publication No. WO 2011/023700

International Patent Application Publication No. WO 2011/063157

International Patent Application Publication No. WO 2012/038390

International Patent Application Publication No. WO 2012/103261

International Patent Application Publication No. WO 2012/103263

Abbott, D. A., Zelle, R. M., Pronk, J. T. and van Maris, A. J. A. (2009) Metabolic engineering of *Saccharomyces cerevisiae* for production of carboxylic acid: current status and challenges. *FEMS Yeast Res.* 9, 1123-1136.

Abdel-Banat, B. M., Nonklang, S., Hoshida, H., and Akada, R. (2010) Random and targeted gene integrations through the control of non-homologous end joining in the yeast *Kluyveromyces marxianus, Yeast* 27, 29-39.

Altschul, S. F., Gish, W., Miller, W., Myers, E. W., and Lipman, D. J. (1990) Basic local alignment search tool, *J Mol Biol* 215, 403-410.

Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs, *Nucleic Acids Res* 25, 3389-3402.

Anderlund, M., Nissen, T. L., Nielsen, J., Villadsen, J., Rydstrom, J., Hahn-Hagerdal, B., and Kielland-Brandt, M. C. (1999) Expression of the *Escherichia coli* pntA and pntB genes, encoding nicotinamide nucleotide transhydrogenase, in *Saccharomyces cerevisiae* and its effect on product formation during anaerobic glucose fermentation, *Appl Environ Microbiol* 65, 2333-2340.

Avalos, J. L., fink, G. R., and Stephanopoulos, G. (2013) Compartmentalization of metabolic pathways in yeast mitochondria improves the production of branched-chain alcohols. *Nat Biotechnol* 31, 335-341.

Booth, L. N., Tuch, B. B., and Johnson, A. D. (2010) Intercalation of a new tier of transcription regulation into an ancient circuit, *Nature* 468, 959-963.

Camarasa, C., Faucet, V., and Dequin, S. (2007) Role in anaerobiosis of the isoenzymes for *Saccharomyces cerevisiae* fumarate reductase encoded by OSM1 and FRDS1, *Yeast* 24, 391-401.

Cao, Z., Song, P., Xu, Q., Su, R., and Zhu, G. (2011) Overexpression and biochemical characterization of soluble pyridine nucleotide transhydrogenase from *Escherichia coli, FEMS Microbiol Lett* 320, 9-14.

Coves, J., Niviere, V., Eschenbrenner, M., and Fontecave, M. (1993) NADPH-sulfite reductase from *Escherichia coli*. A flavin reductase participating in the generation of the free radical of ribonucleotide reductase, *J Biol Chem* 268, 18604-18609.

Cox, S. J., Shalel Ievanon, S., Sanchez, A., Lin, H., Peercy, B., Bennett, G. N., and San, K. Y. (2006) Development of a metabolic network design and optimization framework incorporating implementation constraints: a succinate production case study. *Metab Eng* 8, 46-57.

de Klerck, J.-L. (2010) Succinic acid production by wine yeasts, in Department of Citiculture and Oenology, pp. 1-156, Stellenbosch University.

Dujon, B., Sherman, D., Fischer, G., Durrens, P., Casaregola, S., Lafontaine, I., De Montigny, J., Marck, C., Neuveglise, C., Talla, E., Goffard, N., Frangeul, L., Aigle, M., Anthouard, V., Babour, A., Barbe, V., Barnay, S., Blanchin, S., Beckerich, J. M., Beyne, E., Bleykasten, C., Boisrame, A., Boyer, J., Cattolico, L., Confanioleri, F., De Daruvar, A., Despons, L., Fabre, E., Fairhead, C., Ferry-Dumazet, H., Groppi, A., Hantraye, F., Hennequin, C., Jauniaux, N., Joyet, P., Kachouri, R., Kerrest, A., Koszul, R., Lemaire, M., Lesur, I., Ma, L., Muller, H., Nicaud, J. M., Nikolski, M., Oztas, S., Ozier-Kalogeropoulos, O., Pellenz, S., Potier, S., Richard, G. F., Straub, M. L., Suleau, A., Swennen, D., Tekaia, F., Wesolowski-Louvel, M., Westhof, E., Wirth, B., Zeniou-Meyer, M., Zivanovic, I., Bolotin-Fukuhara, M., Thierry, A., Bouchier, C., Caudron, B., Scarpelli, C., Gaillardin, C., Weissenbach, J., Wincker, P., and Souciet, J. L. (2004) Genome evolution in yeasts, *Nature* 430, 35-44.

Easlon, E., Tsang, F., Skinner, C., Wang, C., and Lin, S. J. (2008) The malate-aspartate NADH shuttle components are novel metabolic longevity regulators required for calorie restriction-mediated life span extension in yeast, *Genes Dev* 22, 931-944.

Eschenbrenner, M., Coves, J., and Fontecave, M. (1995) The flavin reductase activity of the flavoprotein component of sulfite reductase from *Escherichia coli*. A new model for the protein structure, *J Biol Chem* 270, 20550-20555.

Galan, B., Manso, I., Kolb, A., Garcia, J. L., and Prieto, M. A. (2008) The role of FIS protein in the physiological control of the expression of the *Escherichia coli* meta-hpa operon, *Microbiology* 154, 2151-2160.

Grabar, T. B., Zhou, S., Shanmugam, K. T., Yomano, L. P., and Ingram, L. O. (2006) Methylglyoxal bypass identified as source of chiral contamination in l(+) and d(−)-lactate fermentations by recombinant *Escherichia coli, Biotechnol Lett* 28, 1527-1535.

Heerde, E., and Radler, F. (1978) Metabolism of the Anaerobic Formation of succininc acid by *Saccharomyces cerevisiae. Archives of Microbiology* 117, 269-276.

Heinisch, J. J., Buchwald, U., Gottachlich, A., Heppler, N., and Rodicio, R. (2010) A tool kit for molecular genetics of *Kluyveromyces lactis* comprising a congenic strain series and a set of versatile vectors. *FEMS Yeast Res* 10, 333-342.

Hurt, E. C., Allison, D. S., Muller, U., and Schatz, G. (1987) Amino-terminal deletions in the presequence of an imported mitochondrial protein block the targeting function and proteolytic cleavage of the presequence at the carboxy terminus. *J Biol chem.* 262, 1420-1424.

Jantama, K., Haupt, M. J., Svoronos, S. A., Zhang, X., Moore, J. C., Shanmugam, K. T., and Ingram, L. O. (2008a) Combining metabolic engineering and metabolic evolution to develop nonrecombinant strains of *Escherichia coli* C that produce succinate and malate, *Biotechnol Bioeng* 99, 1140-1153.

Jantama, K., Zhang, X., Moore, J. C., Shanmugam, K. T., Svoronos, S. A., and Ingram, L. O. (2008b) Eliminating side products and increasing succinate yields in engineered strains of *Escherichia coli* C, *Biotechnol Bioeng* 101, 881-893.

Jarboe, L. R., Zhang, X., Wang, X., Moore, J. C., Shanmugam, K. T., and Ingram, L. O. (2010) Metabolic engineering for production of biorenewable fuels and chemicals: contributions of synthetic biology, *J Biomed Biotechnol* 2010, 761042.

Kegel, A., Martinez, P., Carter, S. D., and Astrom, S. U. (2006) Genome wide distribution of illegitimate recombination events in *Kluyveromyces lactis, Nucleic Acids Res* 34, 1633-1645.

Kunioka, M., Ninomiya, F., and Funabashi, M. (2009) Biodegradation of poly(butylene succinate) powder in a controlled compost at 58 degrees C. evaluated by naturally-occurring carbon 14 amounts in evolved CO(2) based on the ISO 14855-2 method, *Int J Mol Sci* 10, 4267-4283.

Lee, Y. J., Burlet, E., Galiano, F., Circu, M. L., Aw, T. Y., Williams, B. J., and Witt, S. N. (2011) Phosphate and succinate use different mechanisms to inhibit sugar-induced cell death in yeast: insight into the Crabtree effect, *J Biol Chem* 286, 20267-20274.

Lee, K. S., Kim, J. S., Heo, P., Yang, T. J., Sung, Y. J., Cheon, Y., Koo, H. M., Yu, B. J., Seo, J. H., Jin, Y. S., Park, J. C., and Kweon, D. H. (2012) Characterization of *Saccharomyces cerevisiae* promoters for heterologous gene expression in *Kluyveromyces marxianus, Appl Microbiol Biotechnol*.

Louie, T. M., Yang, H., Karnchanaphanurach, P., Xie, X. S., and Xun, L. (2002) FAD is a preferred substrate and an inhibitor of *Escherichia coli* general NAD(P)H:flavin oxidoreductase, *J Biol Chem* 277, 39450-39455.

Louie, T. M., Xie, X. S., and Xun, L. (2003) Coordinated production and utilization of FADH2 by NAD(P)H-flavin oxidoreductase and 4-hydroxyphenylacetate 3-monooxygenase, *Biochemistry* 42, 7509-7517.

Nair, N. U. and Zhao, H. M. (2009) Mutagenic inverted repeat assisted genome engineering (MIRAGE). *Nucleic Acids Res* 37, e9.

Neupert, W., and Herrmann, J. M. (2007) Translocation of proteins into mitochondria, *Annu Rev Biochem* 76, 723-749.

Neves, L., Oliveira, R. and Lucas, C. (2004) Yeast orthologues with glycerol transport and metabolism. *FEMS Yeast Res* 5, 51-62.

Niu, W., Draths, K. M., and Frost, J. W. (2002) Benzene-free synthesis of adipic acid, *Biotechnol Prog* 18, 201-211.

Nissen, T. L., Anderlund, M., Nielsen, J., Villadsen, J., and Kielland-Brandt, M. C. (2001) Expression of a cytoplasmic transhydrogenase in *Saccharomyces cerevisiae* results in formation of 2-oxoglutarate due to depletion of the NADPH pool, *Yeast* 18, 19-32.

Niviere, V., Fieschi, F., Decout, J. L., and Fontecave, M. (1999) The NAD(P)H:flavin oxidoreductase from *Escherichia coli*. Evidence for a new mode of binding for reduced pyridine nucleotides, *J Biol Chem* 274, 18252-18260.

Oura, E. (1977) Reaction products of yeast fermentations, *Process Biochemistry* 12, 19-21.

Palmieri, L., Vozza, A., Honlinger, A., Dietmeier, K., Palmisano, A., Zara, V., and Palmieri, F. (1999) The mitochondrial dicarboxylate carrier is essnetial for the growth of *Saccharaomyces cerevisiae* on ethnaol or acetate as the sole carbon source. *Mol Microbiol* 31. 569-577.

Palmieri, L., Lasorsa, F. M., Vozza, A., Agrimi, G., Fiermonte, G., Runswick, M. J., Walker, J. E., and Palmieri, F. (2000) Identification and functions of new transporters in yeast mitochondria, *Biochim Biophys Acta* 1459, 363-369.

Papagianni, M. (2007) Advances in citric acid fermentation by *Aspergillus niger*: biochemical aspects, membrane transport and modeling, *Biotechnol Adv* 25, 244-263.

Patel, M. A., Ou, M. S., Harbrucker, R., Aldrich, H. C., Buszko, M. L., Ingram, L. O., and Shanmugam, K. T. (2006) Isolation and characterization of acid-tolerant, thermophilic bacteria for effective fermentation of biomass-derived sugars to lactic acid, *Appl Environ Microbiol* 72, 3228-3235.

Raab, A. M. and Lang, C. (2011) Oxidative versus reductive succinic acid production in the yeast *Saccharomyces cerevisiae. Bioengineered Bugs* 2, 120-123.

Raab, A. M., Gebhardt, G., Bolotina, N., Weuster-Botz, D., and Lang, C. (2010) Metabolic engineering of *Saccharomyces cerevisiae* for the biotechnological production of succinic acid. *Metabolic Engineering*. 12: 518-525.

Raab, A. M., Hlavacek, V., Bolotina, N., and Lang, C. (2011) Shifting the fermentative/oxidative balance in *Saccharomyces cerevisiae* by transcriptional deregulation of the Snf1 upstream activating kinase Sak1p. *Applied and Environmental Microbiology*. 77: 1981-1989.

Roa Engel, C. A., Straathof, A. J., Zijlmans, T. W., van Gulik, W. M., and van der Wielen, L. A. (2008) Fumaric acid production by fermentation, *Appl Microbiol Biotechnol* 78, 379-389.

Robinson, K. M., and Lemire, B. D. (1996) Covalent attachment of FAD to the yeast succinate dehydrogenase flavoprotein requires import into mitochondria, presequence removal, and folding, *J Biol Chem* 271, 4055-4060.

Roper, D. I., Fawcett, T., and Cooper, R. A. (1993) The *Escherichia coli* C homoprotocatechuate degradative operon: hpc gene order, direction of transcription and control of expression, *Mol Gen Genet* 237, 241-250.

Rusche, L. N., and Rine, J. (2010) Switching the mechanism of mating type switching: a domesticated transposase supplants a domesticated homing endonuclease, *Genes Dev* 24, 10-14.

Saliola, M., Bartoccioni, P. C., De Maria, I., Lodi, T., and Falcone, C. (2004) The deletion of the succinate dehydrogenase gene KlSDH1 in *Kluyveromyces lactis* does not lead to respiratory deficiency, *Eukaryot Cell* 3, 589-597.

Saliola, M., Sponziello, M., D'Amici, S., Lodi, T., Falcone, C. (2008) Characterization of KlGUT2, a gene of the glycerol-3-phosphate shuttle, in *Kluyveromyces lactis. FEMS Yeast Res* 8, 697-705.

Shao, Z., Luo, Y., and Zhao, H. (2012) DNA assembler method for construction of zeaxanthin-producing strains of *Saccharomyces cerevisiae, Methods Mol Biol* 898, 251-262.

Stein, I., Peleg, Y., Even-Ram, S., and Pines, O. (1994) The single translation product of the FUM1 gene (fumarase) is processed in mitochondria before being distributed between the cytosol and mitochondria in *Saccharomyces cerevisiae, Mol Cell Biol* 14, 4770-4778.

Sun, J., Shao, Z., Zhao, H., Nair, N., Wen, F., and Xu, J. H. (2012) Cloning and characterization of a panel of constitutive promoters for applications in pathway engineering in *Saccharomyces cerevisiae, Biotechnol Bioeng* 109, 2082-2092.

Tiwari, M. K., Singh, R. K., Lee, J. K., and Zhao, H. (2012) Mechanistic studies on the flavin:NADH reductase (PrnF) from *Pseudomonas fluorescens* involved in arylamine oxygenation, *Bioorg Med Chem Lett* 22, 1344-1347.

van Maris, A. J., Winkler, A. A., Porro, D., van Dijken, J. P., and Pronk, J. T. (2004) Homofermentative lactate production cannot sustain anaerobic growth of engineered *Saccharomyces cerevisiae*: possible consequence of energy-dependent lactate export, *Appl Environ Microbiol* 70, 2898-2905.

Vemuri, G. N., Eiteman, M. A., and altman, E. (2002) Effects of growth mode and pyruvate carboxylase on succinic acid production by metabolically engineered strains of *Escherichia coli*, *App Enivron Microbiol* 68, 1715-1727.

Vogtel, F. N., Wortelkamp, S., Zahedi, R. P., Becker, D., Leidhold, C., Gevaert, K., Kellermann, J., voos, W., Sickmann, A., Pfanner, N., and Meisinger, C. (2009) global analysis of the mitochondrial N-proteome idnetifies a processing peptidase critical fro protein stability. *Cell* 139, 428-439.

Wach, A., Brachat, A., Pohlmann, R., and Philippsen, P. (1994) New heterologous modules for classical or PCR-based gene disruptions in *Saccharomyces cerevisiae*, *Yeast* 10, 1793-1808.

Wang, Q., Ingram, L. O., and Shanmugam, K. T. (2011) Evolution of D-lactate dehydrogenase activity from glycerol dehydrogenase and its utility for D-lactate production from lignocellulose, *Proc Natl Acad Sci USA* 108, 18920-18925.

Xu, G., Liu, L. and Chen, J. (2012) Reconstruction of cytosolic fumaric acid biosynthetic pathways in *Saccharomyces cerevisiae*. *Microbial Cell Factories* 11, 24-34.

Yuzbashev, T. V., Yuzbasheva, E. Y., Laptev, I. A., Sobolevskaya, T. I., Vybornaya, T. V., Larina, A. S., Gvilava, I. T., Antonova, S. V. and Sineoky, S. P. (2011) Is it possible to produce succinic acid at low pH? *Bioengineered Bugs* 2, 115-119.

Zelle, R. M., de Hulster, E., van Winden, W. A., de Waard, P., Dijkema, C., Winkler, A. A., Geertman, J. M., van Dijken, J. P., Pronk, J. T., and van Maris, A. J. (2008) Malic acid production by *Saccharomyces cerevisiae*: engineering of pyruvate carboxylation, oxaloacetate reduction, and malate export, *Appl Environ Microbiol* 74, 2766-2777.

Zhang, Q., Zhang, L., Ding, Z., and Shi, G. (2011) Metabolic engineering of wild acid-resistant yeast for L-lactic acid production. *Chin. J. Biotech.* 27, 1024-1031.

Zhang, X., Jantama, K., Moore, J. C., Jarboe, L. R., Shanmugam, K. T., and Ingram, L. O. (2009a) Metabolic evolution of energy-conserving pathways for succinate production in *Escherichia coli*, *Proc Natl Acad Sci USA* 106, 20180-20185.

Zhang, X., Jantama, K., Shanmugam, K. T., and Ingramb, L. O. (2009) Reengineering *Escherichia coli* for Succinate Production in Mineral Salts Medium, *Appl Environ Microbiol* 75, 7807-7813.

Zhu, L. W., Li, X. H. M., Liu, J. H., Yuan, Z. P., Chen, T., and Tang, Y. J. (2013) Activation of glyoxylate pathway without the activation of its related gene in succinate-producing engineered *Escherichia coli*, *Meab. Eng* 20C, 9-19.

TABLE 1

Sequence Information

| Seq ID No. | Primer/ Plasmid Name | Sequence/ Description |
|---|---|---|
| 1 | SD123 | 5'-GGAAGTAAAAGTCGTAACAAGG-3' |
| 2 | SD124 | 5'-CGCCAGTTCTGCTTACC-3' |
| 3 | SD125 | 5'-GCATATCAATAAGCGGAGGAAAAG-3' |
| 4 | SD126 | 5'-GGTCCGTGTTTCAAGACGG-3' |
| 5 | SD127 | 5'-TCCGTAGGTGAACCTGCGG-3' |
| 6 | SD128 | 5'-TCCTCCGCTTATTGATATGC-3' |
| 7 | SD129 | 5'-CTTGTTCGCTATCGGTCTC-3' |
| 8 | SD130 | 5'-GAGACCGATAGCGAACAAG-3' |
| 9 | SD336 | CACCAGTAAAACATACGCATACACATACAC |
| 10 | SD343 | AAGCTTGTGTATATGCCAAATAAAGTAAAA |
| 11 | SD390 | CAATGCGAATAGCACCAGTGAGAGCACCAG |
| 12 | SD392 | AACAAGACCAAACTCATCCCCTCCGAAGAA |
| 13 | pSD57 | pSD57, a plasmid designed to supply a linear DNA fragment for integrating a lactate dehydrogenase expression cassette into strain SD98, and for simultaneously deleting the PDC1 coding region. |
| 14 | pSD59 | pSD59fumC, a plasmid designed to supply a linear DNA fragment for integrating a cassette containing four genes needed for the reductive pathway to succinate into strain SD98, and for simultaneously deleting the PDC1 coding region. |

TABLE 2

Genes used for succinate production cassette of SD631

| Gene (coding region) | Source | Promoter used | Terminator used |
|---|---|---|---|
| pck (PEP carboxykinase) | *E. coli* C | KmPDC1 | ScTEF1 |
| mdh (malate dehydrogenase) | *E. coli* C | ScTPI1 | ScTPI1 |
| fumC (fumarase) | *E. coli* C | ScGPM1 | ScGPM1 |
| FRD1 (fumarate reductase) | *S. cerevisiae* | ScTEF1 | KmPDC1 |

What is claimed is:

1. A genetically engineered yeast cell of genus *Kluyveromyces*, tolerant to organic acid at low pH, and comprising one or more exogenous genes encoding cytosolic enzymes necessary for reductive pathway from phosphoenol pyruvate to succinate,
    wherein said cystolic enzymes are selected from the group consisting of phosphoenol pyruvate carboxykinase of EC 4.1.1.49, malate dehydrogenase of EC 1.1.1.37, fumarase of EC 4.2.1.2 and fumarate reductase of EC 1.3.1.6,
    at least one of said exogenous genes is inserted at the pyruvate decarboxylase locus, and
    the genetically engineered yeast cell is capable of producing succinate under anaerobic or microaerobic conditions from phosphoenol pyruvate.

2. The genetically engineered yeast cell of claim 1, further comprising an enzyme selected from the group consisting of pyruvate carboxylase and phosphoenol pyruvate carboxylase.

3. The genetically engineered yeast cell of claim 1, further comprising one or more of genes encoding cytosolic enzymes necessary for oxidative pathway from phosphoenol pyruvate to succinate.

4. The genetically engineered yeast cell of claim 3, wherein one or more of genes encoding said cytoplasmic enzymes necessary for both oxidative and reductive pathways from phosphoenol pyruvate to succinate are derived from yeast of the genera *Saccharomyes, Kluyveromyces, Candida, Pichia, Hansenula* or *Issatchenkia*.

5. The genetically engineered yeast cell of claim 3, wherein one or more genes encoding said cytoplasmic enzymes necessary for both oxidative and reductive pathways from phosphoenol pyruvate to succinate are derived from bacterial genes.

6. The genetically engineered yeast cell of claim 3, wherein one or more genes encoding said cytoplasmic enzymes necessary for both oxidative and reductive pathways from phosphoenol pyruvate to succinate are derived from bacteria of the genera *Escherichia, Actinobacillus, Mannheimia,* or *Basfia*.

7. The genetically engineered yeast cell of claim 3, wherein one or more genes encoding said cytoplasmic enzymes necessary for both oxidative and reductive pathways from phosphoenol pyruvate to succinate are derived from *Escherichia coli* genes.

8. The genetically engineered yeast cell of claim 3, wherein said oxidative pathway and reductive pathway operate without the use of an enzyme of the glyoxylate shunt.

9. The genetically engineered yeast cell of claim 3, wherein said cytoplasmic enzymes necessary for oxidative pathway from phosphoenol pyruvate to succinate are selected from the group consisting of pyruvate kinase, pyruvate dehydrogenase, citrate synthase, aconitase, isocitrate dehydrogenase, alpha-keto glutarate dehydrogenase and succinyl-CoA synthetase.

10. The genetically engineered yeast cell of claim 1, wherein said fumarase does not comprise an iron-sulfur cluster.

11. The genetically engineered yeast cell of claim 10, wherein said fumarase is encoded by *Escherichia coli* fumC gene.

12. The genetically engineered yeast cell of claim 1, further comprising a mutation in a dicarboxylate transporter responsible for the transport of succinate from cytoplasm into mitochondria, wherein said dicarboxylate transporter is encoded by a DIC1 gene or a SFC1 gene.

13. A method of producing succinate, the method comprising growing the genetically engineered yeast cell of claim 1, and harvesting said succinate.

14. The genetically engineered yeast cell of claim 1, wherein said one or more genes are derived from a yeast strain.

15. The genetically engineered yeast cell of claim 1, wherein said one or more genes are derived from a bacterial strain.

16. The genetically engineered yeast cell of claim 1, wherein said one or more genes are derived from a yeast strain of the genera *Saccharomyces, Kluyveromyces, Pichia, Hansenula* or *Issatchenkia*.

17. The genetically engineered yeast cell of claim 1, wherein said one or more genes are derived from a bacterial cell of the genera *Escherichia, Actinobacillus, Mannheimia,* or *Basfia*.

18. The genetically engineered yeast cell of claim 1, wherein said one or more genes are derived from a strain of *Escherichia coli*.

19. The genetically engineered yeast cell of claim 1, which is of species *Kluyveromyces marxianus*.

20. The genetically engineered yeast cell of claim 1, which comprises one or more exogenous genes encoding phosphoenol pyruvate carboxykinase of EC 4.1.1.49, malate dehydrogenase of EC 1.1.1.37, fumarase of EC 4.2.1.2 and fumarate reductase of EC 1.3.1.6.

21. The genetically engineered yeast cell of claim 1, which is of species *Kluyveromyces marxianus*, and which comprises one or more exogenous genes encoding phosphoenol pyruvate carboxykinase of EC 4.1.1.49, malate dehydrogenase of EC 1.1.1.37, fumarase of EC 4.2.1.2 and fumarate reductase of EC 1.3.1.6.

22. The genetically engineered yeast cell of claim 1, which, when grown microaerobically in a 200 ml fermentor at 37° C. and pH 5 using a medium comprising 100 g/L glucose, and supplemented with 10 µg/L biotin, 1 mg/L niacin, and 1 mg/L thiamine hydrochloride, produces more succinate per hour than a cell that is the same other than not comprising said one or more exogenous genes.

23. The genetically engineered yeast cell of claim 1, which is of species *Kluyveromyces marxianus*, and which, when grown microaerobically in a 200 ml fermentor at 37° C. and pH 5 using a medium comprising 100 glucose, and supplemented with 1.0 µg/L biotin, 1 mg/L niacin, and 1 mg/L thiamine hydrochloride, produces more succinate per hour than a cell that is the same other than not comprising said one or more exogenous genes.

24. The genetically engineered yeast cell of claim 1, which:
    is of species *Kluyveromyces marxianus*;
    comprises one or more exogenous genes encoding phosphoenol pyruvate carboxykinase of EC 4.1.1.49, malate dehydrogenase of EC 1.1.1.37, fumarase of EC 4.2.1.2 and fumarase reductase of EC 1.3.1.6; and
    when grown microaerobically in a 200 ml fermentor at 37° C. and pH 5 using a medium comprising 100 g/L glucose, and supplemented with 10 µg/L biotin, 1 mg/L niacin, and 1 mg/L thiamine hydrochloride, produces more succinate per hour than a cell that is the same other than not comprising said one or more exogenous genes.

* * * * *

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
```

<223> OTHER INFORMATION: PCR Primer SD123

<400> SEQUENCE: 1
ggaagtaaaa gtcgtaacaa gg                                          22

<210> SEQ ID NO 2
<211> LENGTH: 17
<212> TYPE: DNA
<213> ORGANISM: Artificial Sequence
<220> FEATURE:
<223> OTHER INFORMATION: PCR Primer SD124

<400> SEQUENCE: 2
cgccagttct gcttacc                                                17

<210> SEQ ID NO 3
<211> LENGTH: 24
<212> TYPE: DNA
<213> ORGANISM: Artificial Sequence
<220> FEATURE:
<223> OTHER INFORMATION: PCR Primer SD125

<400> SEQUENCE: 3
gcatatcaat aagcggagga aaag                                        24

<210> SEQ ID NO 4
<211> LENGTH: 19
<212> TYPE: DNA
<213> ORGANISM: Artificial Sequence
<220> FEATURE:
<223> OTHER INFORMATION: PCR Primer SD126

<400> SEQUENCE: 4
ggtccgtgtt tcaagacgg                                              19

<210> SEQ ID NO 5
<211> LENGTH: 19
<212> TYPE: DNA
<213> ORGANISM: Artificial Sequence
<220> FEATURE:
<223> OTHER INFORMATION: PCR Primer SD127

<400> SEQUENCE: 5
tccgtaggtg aacctgcgg                                              19

<210> SEQ ID NO 6
<211> LENGTH: 20
<212> TYPE: DNA
<213> ORGANISM: Artificial Sequence
<220> FEATURE:
<223> OTHER INFORMATION: PCR Primer SD128

<400> SEQUENCE: 6
tcctccgctt attgatatgc                                             20

<210> SEQ ID NO 7
<211> LENGTH: 19
<212> TYPE: DNA
<213> ORGANISM: Artificial Sequence
<220> FEATURE:
<223> OTHER INFORMATION: PCR Primer SD129

<400> SEQUENCE: 7
cttgttcgct atcggtctc                                              19

```
<210> SEQ ID NO 8
<211> LENGTH: 19
<212> TYPE: DNA
<213> ORGANISM: Artificial Sequence
<220> FEATURE:
<223> OTHER INFORMATION: PCR Primer SD130

<400> SEQUENCE: 8
gagaccgata gcgaacaag                                                   19

<210> SEQ ID NO 9
<211> LENGTH: 30
<212> TYPE: DNA
<213> ORGANISM: Artificial Sequence
<220> FEATURE:
<223> OTHER INFORMATION: PCR Primer SD336

<400> SEQUENCE: 9
caccagtaaa acatacgcat acacatacac                                       30

<210> SEQ ID NO 10
<211> LENGTH: 30
<212> TYPE: DNA
<213> ORGANISM: Artificial Sequence
<220> FEATURE:
<223> OTHER INFORMATION: PCR Primer SD343

<400> SEQUENCE: 10
aagcttgtgt atatgccaaa taaagtaaaa                                       30

<210> SEQ ID NO 11
<211> LENGTH: 30
<212> TYPE: DNA
<213> ORGANISM: Artificial Sequence
<220> FEATURE:
<223> OTHER INFORMATION: PCR Primer SD390

<400> SEQUENCE: 11
caatgcgaat agcaccagtg agagcaccag                                       30

<210> SEQ ID NO 12
<211> LENGTH: 30
<212> TYPE: DNA
<213> ORGANISM: Artificial Sequence
<220> FEATURE:
<223> OTHER INFORMATION: PCR Primer SD392

<400> SEQUENCE: 12
aacaagacca aactcatccc ctccgaagaa                                       30

<210> SEQ ID NO 13
<211> LENGTH: 10036
<212> TYPE: DNA
<213> ORGANISM: Artificial Sequence
<220> FEATURE:
<223> OTHER INFORMATION: Plasmid  pSD57

<400> SEQUENCE: 13
cccgggaatc tcggtcgtaa tgatttttat aatgacgaaa aaaaaaaaat tggaaagaaa       60
aagctttaat gcggtagttt atcacagtta aattgctaac gcagtcaggc accgtgtatg      120
aaatctaaca atgcgctcat cgtcatcctc ggcaccgtca ccctggatgc tgtaggcata      180
ggcttggtta tgccggtact gccgggcctc ttgcgggata tcgtccattc cgacagcatc      240
gccagtcact atggcgtgct gctagcgcta tatgcgttga tgcaatttct atgcgcaccc      300
```

```
gttctcggag cactgtccga ccgctttggc cgccgcccag tcctgctcgc ttcgctactt    360
ggagccacta tcgactacgc gatcatggcg accacacccg tcctgtggat cctctacgcc    420
ggacgcatcg tggccggcat caccggcgcc acaggtgcgg ttgctggcgc ctatatcgcc    480
gacatcaccg atgggaaga tcgggctcgc cacttcgggc tcatgagcgc ttgtttcggc     540
gtgggtatgg tggcaggccc cgtggccggg gactgttgg gcgccatctc cttgcatgca     600
ccattccttg cggcggcggt gctcaacggc ctcaacctac tactgggctg cttcctaatg    660
caggagtcgc ataagggaga gcgtcgaccg atgcccttga gagccttcaa cccagtcagc    720
tccttccggt gggcgcgggg catgactatc gtcgccgcac ttatgactgt cttctttatc    780
atgcaactcg taggacaggt gccggcagcg ctctgggtca ttttcggcga ggaccgcttt    840
cgctggagcg cgacgatgat cggcctgtcg cttgcggtat tcggaatctt gcacgccctc    900
gctcaagcct tcgtcactgg tcccgccacc aaacgtttcg gcgagaagca ggccattatc    960
gccggcatgg cggccgacgc gctgggctac gtcttgctgg cgttcgcgac gcgaggctgg   1020
atggccttcc ccattatgat tcttctcgct tccggcggca tcgggatgcc cgcgttgcag   1080
gccatgctgt ccaggcaggt agatgacgac catcagggac agcttcaagg atcgctcgcg   1140
gctcttacca gcctaacttc gatcactgga ccgctgatcg tcacggcgat ttatgccgcc   1200
tcggcgagca catggaacgg gttggcatgg attgtaggcg ccgccctata ccttgtctgc   1260
ctccccgcgt tgcgtcgcgg tgcatggagc cgggccacct cgacctgaat ggaagccggc   1320
ggcacctcgc taacggattc accactccaa gaattggagc caatcaattc ttgcggagaa   1380
ctgtgaatgc gcaaaccaac ccttggcaga acatatccat cgcgtccgcc atctccagca   1440
gccgcacgcg gcgcatctcg ggcagcgttg gtcctggcc acgggtgcgc atgatcgtgc     1500
tcctgtcgtt gaggacccgg ctaggctggc ggggttgcct tactggttag cagaatgaat   1560
caccgatacg cgagcgaacg tgaagcgact gctgctgcaa acgtctgcg acctgagcaa     1620 caacatgaat ggtcttcggt ttccgtgttt cgtaaagtct ggaaacgcgg aagtcagcgc   1680
cctgcaccat tatgttccgg atctgcatcg caggatgctg ctggctaccc tgtggaacac   1740
ctacatctgt attaacgaag cgctggcatt gaccctgagt gattttctc tggtcccgcc    1800 gcatccatac cgccagttgt ttaccctcac aacgttccag taaccgggca tgttcatcat   1860
cagtaacccg tatcgtgagc atcctctctc gtttcatcgg tatcattacc cccatgaaca   1920
gaaattcccc cttacacgga ggcatcaagt gaccaaacag gaaaaaaccg cccttaacat   1980
ggcccgcttt atcagaagcc agacattaac gcttctggag aaactcaacg agctggacgc   2040
ggatgaacag gcagacatct gtgaatcgct tcacgaccac gctgatgagc tttaccgcag   2100
ctgcctcgcg cgtttcggtg atgacggtga aaacctctga cacatgcagc tcccggagac   2160
ggtcacagct tgtctgtaag cggatgccgg gagcagacaa gcccgtcagg gcgcgtcagc   2220
gggtgttggc gggtgtcggg gcgcagccat gacccagtca cgtagcgata gcggagtgta   2280
tactggctta actatgcggc atcagagcag attgtactga gagtgcacca tatgcggtgt   2340
gaaataccgc acagatgcgt aaggagaaaa taccgcatca ggcgctcttc cgcttcctcg   2400
ctcactgact cgctgcgctc ggtcgttcgg ctgcggcgag cggtatcagc tcactcaaag   2460
gcggtaatac ggttatccac agaatcaggg gataacgcag gaaagaacat gtgagcaaaa   2520
ggccagcaaa aggccaggaa ccgtaaaaag gccgcgttgc tggcgttttt ccataggctc   2580
cgcccccctg acgagcatca caaaaatcga cgctcaagtc agaggtggcg aaacccgaca   2640
ggactataaa gataccaggc gtttccccct ggaagctccc tcgtgcgctc tcctgttccg   2700
```

```
accctgccgc ttaccggata cctgtccgcc tttctcccttt cgggaagcgt ggcgctttct    2760
catagctcac gctgtaggta tctcagttcg gtgtaggtcg ttcgctccaa gctgggctgt    2820
gtgcacgaac cccccgttca gcccgaccgc tgcgccttat ccggtaacta tcgtcttgag    2880
tccaacccgg taagacacga cttatcgcca ctggcagcag ccactggtaa caggattagc    2940
agagcgaggt atgtaggcgg tgctacagag ttcttgaagt ggtggcctaa ctacggctac    3000
actagaagga cagtatttgg tatctgcgct ctgctgaagc cagttacctt cggaaaaaga    3060
gttggtagct cttgatccgg caaacaaacc accgctggta gcggtggttt ttttgtttgc    3120
aagcagcaga ttacgcgcag aaaaaaagga tctcaagaag atcctttgat cttttctacg    3180
gggtctgacg ctcagtggaa cgaaaactca cgttaaggga ttttggtcat gagattatca    3240
aaaaggatct tcacctagat ccttttaaat taaaaatgaa gttttaaatc aatctaaagt    3300
atatatgagt aaacttggtc tgacagttac caatgcttaa tcagtgaggc acctatctca    3360
gcgatctgtc tatttcgttc atccatagtt gcctgactcc ccgtcgtgta gataactacg    3420
atacgggagg gcttaccatc tggccccagt gctgcaatga taccgcgaga cccacgctca    3480
ccggctccag atttatcagc aataaaccag ccagccggaa gggccgagcg cagaagtggt    3540
cctgcaactt tatccgcctc catccagtct attaattgtt gccgggaagc tagagtaagt    3600
agttcgccag ttaatagttt gcgcaacgtt gttgccattg ctgcaggcat cgtggtgtca    3660
cgctcgtcgt ttggtatggc ttcattcagc tccggttccc aacgatcaag gcgagttaca    3720
tgatccccca tgttgtgcaa aaaagcggtt agctccttcg gtcctccgat cgttgtcaga    3780
agtaagttgg ccgcagtgtt atcactcatg gttatggcag cactgcataa ttctcttact    3840
gtcatgccat ccgtaagatg cttttctgtg actggtgagt actcaaccaa gtcattctga    3900
gaatagtgta tgcggcgacc gagttgctct tgcccggcgt caacacggga taataccgcg    3960
ccacatagca gaactttaaa agtgctcatc attggaaaac gttcttcggg gcgaaaactc    4020
tcaaggatct taccgctgtt gagatccagt tcgatgtaac ccactcgtgc acccaactga    4080
tcttcagcat cttttacttt caccagcgtt tctgggtgag caaaaacagg aaggcaaaat    4140
gccgcaaaaa agggaataag ggcgacacgg aaatgttgaa tactcatact cttcctttttt    4200
caatattatt gaagcattta tcagggttat tgtctcatga gcggatacat atttgaatgt    4260
atttagaaaa ataaacaaat aggggttccg cgcacatttc cccgaaaagt gccacctgac    4320
gtctaagaaa ccattattat catgacatta acctataaaa ataggcgtat cacgaggccc    4380
tttcgtcttc aagaattctg aaccagtcct aaaacgagta aataggaccg gcaattcttc    4440
aagcaataaa caggaatacc aattattaaa agataactta gtcagatcgt acaataaagc    4500
tttgaagaaa aatgcgcctt attcaatctt tgctataaaa aatggcccaa aatctcacat    4560
tggaagacat tgatgacct catttctttc aatgaagggc ctaacggagt tgactaatgt    4620
tgtgggaaat tggagcgata agcgtgcttc tgccgtggcc aggacaacgt atactcatca    4680
gataacagca ataccctgatc actacttcgc actagtttct cggtactatg catatgatcc    4740
aatatcaaag gaaatgatag cattgaagga tgagactaat ccaattgagg agtggcagca    4800
tatagaacag ctaaagggta gtgctgaagg aagcatacga taccccgcat ggaatgggat    4860
aatatcacag gaggtactag actacctttc atcctacata aatagacgca tataagtacg    4920
catttaagca taaacacgca ctatgccgtt cttctcatgt atatatatat acaggcaaca    4980
cgcagatata ggtgcgacgt gaacagtgag ctgtatgtgc gcagctcgcg ttgcatttttc    5040
```

```
ggaagcgctc gttttcggaa acgctttgaa gttcctattc cgaagttcct attctctaga    5100
aagtatagga acttcagagc gcttttgaaa accaaaagcg ctctgaagac gcactttcaa    5160
aaaaccaaaa acgcaccgga ctgtaacgag ctactaaaat attgcgaata ccgcttccac    5220
aaacattgct caaaagtatc tctttgctat atatctctgt gctatatccc tatataacct    5280
acccatccac ctttcgctcc ttgaacttgc atctaaactc gacctctaca tttttatgt     5340 ttatctctag tattactctt tagacaaaaa aattgtagta agaactattc atagagtgaa    5400
tcgaaaacaa tacgaaaatg taaacatttc ctatacgtag tatatagaga caaaatagaa    5460
gaaaccgttc ataattttct gaccaatgaa gaatcatcaa cgctatcact ttctgttcac    5520
aaagtatgcg caatccacat cggtatagaa tataatcggg gatgccttta tcttgaaaaa    5580
atgcacccgc agcttcgcta gtaatcagta acgcgggaa gtggagtcag cttttttta     5640 tggaagagaa aatagacacc aaagtagcct tcttctaacc ttaacggacc tacagtgcaa    5700
aaagttatca agagactgca ttatagagcg cacaaaggag aaaaaagta atctaagatg     5760 ctttgttaga aaaatagcgc tctcgggatg cattttgta gaacaaaaaa gaagtataga    5820
ttctttgttg gtaaaatagc gctctcgcgt tgcatttctg ttctgtaaaa atgcagctca    5880 gattcttgt ttgaaaaatt agcgctctcg cgttgcattt ttgttttaca aaatgaagc     5940 acagattctt cgttggtaaa atagcgcttt cgcgttgcat ttctgttctg taaaatgca    6000 gctcagattc tttgtttgaa aaattagcgc tctcgcgttg cattttgtt ctacaaaatg     6060 aagcacagat gcttcgttaa caaagatatg ctattgaagt gcaagatgga aacgcagaaa    6120
atgaaccggg gatgcgacgt gcaagattac ctatgcaata gatgcaatag tttctccagg    6180
aaccgaaata catacattgt cttccgtaaa gcgctagact atatattatt atacaggttc    6240
aaatatacta tctgtttcag ggaaaactcc caggttcgga tgttcaaaat tcaatgatgg    6300
gtaacaagta cgatcgtaaa tctgtaaaac agtttgtcgg atattaggct gtatctcctc    6360
aaagcgtatt cgaatatcat tgagaagctg cagcgtcaca tcggataata atgatggcag    6420
ccattgtaga agtgcctttt gcatttctag tctctttctc ggtctagcta gttttactac    6480
atcgcgaaga tagaatctta gatcacactg cctttgctga gctggatcaa tagagtaaca    6540
aaagagtggt aaggcctcgt taaggacaa ggacctgagc ggaagtgtat cgtacagtag     6600
acggagtata ctagtatagt ctatagtccg tggaattctc atgtttgaca gcttatcatc    6660
gataagcttt tcaattcaat tcatcatttt tttttattc tttttttga tttcggtttc     6720 tttgaaattt ttttgattcg gtaatctccg aacagaagga agaacgaagg aaggagcaca    6780
gacttagatt ggtatatata cgcatatgta gtgttgaaga acatgaaat tgcccagtat     6840 tcttaaccca actgcacaga acaaaaacct gcaggcacca gtaaaacata cgcatacaca    6900
tacacacata gagcaagcaa gcaggctagc aaccaggaaa ggctgccagt gactgctact    6960
gggtgtctaa gaaccgtagg gcggattatt gttgcggtgg ttggttgcgg gtggttatgc    7020
gatggtacgg tgcagaatcg tacggtgttg gttatggaat tagtatgggt atgtgatatg    7080
tggtaatatg tgatattggg ttattgtgat ttggaatact gaatatcgaa tatgggatat    7140
ggaatatggc catggcatgg tatggtatgg atgggagta ttctatttta ttttatttta     7200
ttctggttcc tgcgtttagg gtagggtagg aagaaggtga gtgcttttgt atataagtgg    7260
agtgtctgga tcagttttgt ggattgtgaa tgttgttagt ttcccctttta atgtatattt    7320 gtattatttg cttttgagta ctcaataacc aagcacaact actagtttta aaggatccat    7380
cctcttaaac agtacaatcg caaagaaaag ctccacaccc aaaccaaata attgcaatga    7440
```

```
aactcgccgt ttatagcaca aaacagtacg acaagaagta cctgcaacag gtgaacgagt    7500
cctttggctt tgagctggaa ttttttgact ttctgctgac ggaaaaaacc gctaaaactg    7560
ccaatggctg cgaagcggta tgtattttcg taaacgatga cggcagccgc ccggtgctgg    7620
aagagctgaa aaagcacggc gttaaatata tcgccctgcg ctgtgccggt ttcaataacg    7680
tcgaccttga cgcggcaaaa gaactggggc tgaaagtagt ccgtgttcca gcctatgatc    7740
cagaggccgt tgctgaacac gccatcggta tgatgatgac gctgaaccgc cgtattcacc    7800
gcgcgtatca gcgtacccgt gatgctaact tctctctgga aggtctgacc ggctttacta    7860
tgtatggcaa aacggcaggc gttatcgtta ccggtaaaat cggtgtggcg atgctgcgca    7920
ttctgaaagg ttttggtatg cgtctgctgg cgttcgatcc gtatccaagt gcagcggcgc    7980
tggaactcgg tgtggagtat gtcgatctgc aaccctgtt ctctgaatca gacgttatct    8040
ctctgcactg cccgctgaca ccggaaaact atcatctgtt gaacgaagcc gccttcgaac    8100
agatgaaaaa tggcgtgatg atcgtcaata ccagtcgcgg tgcattgatt gattctcagg    8160
cagcaattga agcgctgaaa atcagaaaaa ttggttcgtt gggtatggac gtgtatgaga    8220
acgaacgcga tctattcttt gaagataaat ccaacgacgt gatccaggat gacgtattcc    8280
gtcgcctgtc tgcctgccac aacgtgctgt ttaccgggca ccaggcattc ctgacagcag    8340
aagctctgac cagtatttct cagactacgc tgcaaaactt aagcaatctg gaaaaaggcg    8400
aaacctgccc gaacgaactg gtttaacgta cgctgcaggt cgacggatcc ccgggttaat    8460
taaggcgcgc cagatctgtt tagcttgcct cgtccccgcc gggtcacccg gccagcgaca    8520
tggaggccca gaataccctc cttgacagtc ttgacgtgcg cagctcaggg gcatgatgtg    8580
actgtcgccc gtacatttag cccatacatc cccatgtata atcatttgca tccatacatt    8640
ttgatggccg cacggcgcga agcaaaaatt acggctcctc gctgcagacc tgcgagcagg    8700
gaaacgctcc cctcacagac gcgttgaatt gtccccacgc cgcgcccctg tagagaaata    8760
taaaaggtta ggatttgcca ctgaggttct tctttcatat acttcctttt aaaatcttgc    8820
taggatacag ttctcacatc acatccgaac ataaacaacc atgggtaagg aaaagactca    8880
cgtttcgagg ccgcgattaa attccaacat ggatgctgat ttatatgggt ataaatgggc    8940
tcgcgataat gtcgggcaat caggtgcgac aatctatcga ttgtatggga agcccgatgc    9000
gccagagttg tttctgaaac atggcaaagg tagcgttgcc aatgatgtta cagatgagat    9060
ggtcagacta aactggctga cggaatttat gcctcttccg accatcaagc attttatccg    9120
tactcctgat gatgcatggt tactcaccac tgcgatcccc ggcaaaacag cattccaggt    9180
attagaagaa tatcctgatt caggtgaaaa tattgttgat gcgctggcag tgttcctgcg    9240
ccggttgcat tcgattcctg tttgtaattg tccttttaac agcgatcgcg tatttcgtct    9300
cgctcaggcg caatcacgaa tgaataacgg tttggttgat gcgagtgatt ttgatgacga    9360
gcgtaatggc tggcctgttg aacaagtctg gaaagaaatg cataagcttt tgccattctc    9420
accggattca gtcgtcactc atggtgattt ctcacttgat aaccttattt ttgacgaggg    9480
gaaattaata ggttgtattg atgttggacg agtcggaatc gcagaccgat accaggatct    9540
tgccatccta tggaactgcc tcggtgagtt ttctccttca ttacagaaac ggctttttca    9600
aaaatatggt attgataatc ctgatatgaa taaattgcag tttcatttga tgctcgatga    9660
gttttttcta atcagtactga caataaaaag attcttgttt tcaagaactt gtcatttgta    9720
tagttttttt atattgtagt tgttctattt taatcaaatg ttagcgtgat ttatattttt    9780
```

```
tttcgcctcg acatcatctg cccagatgcg aagttaagtg cgcagaaagt aatatcatgc    9840
gtcaatcgta tgtgaatgct ggtcgctata ctgctgtcga ttcgatacta acgccgccat    9900
ccagtgtcga aaacgagctc gaattcatcg atagagggag aggataaaga gataaattac    9960
gattttggat tttaatgatt ttataaacaa caacaaccaa ccagccttt actttatttg    10020 gcatatacac aagctt                                                   10036

<210> SEQ ID NO 14
<211> LENGTH: 18144
<212> TYPE: DNA
<213> ORGANISM: Artificial Sequence
<220> FEATURE:
<223> OTHER INFORMATION: Plasmid pSD59

<400> SEQUENCE: 14
cgcgtgtcat aaacacggcg gcttctacct cggtagcatc ggcggtccgg cggcggtact      60
ggcgcagcag agcatcaagc atctggagtg cgtcgcttat ccggagctgg gtatggaagc     120
tatctggaaa atcgaagtag aagatttccc ggcgtttatc ctggtcgatg acaaaggtaa     180
cgacttcttc cagcaaatcg tcaacaaaca gtgcgcgaac tgcactaagt aagtctgaag     240
aatgaatgat ttgatgattt ctttttccct ccattttct tactgaatat atcaatgata     300
tagacttgta tagtttatta tttcaaatta gtagctata tatagtcaag ataacgtttg      360
tttgacacga ttcacattat cgtcgacatc ttttttcagc ctgtcgtggt agcaatttga     420
ggagtattat taattgaata ggttcatttt gcgctcgcat aaacagtttt cgtcagggac     480
agtatgttgg aatgagtggt aattaatggt gacatgacat gttatagcaa taaccttgat     540
gtttacatcg tagtttaatg tacaccccgc gaattcgttc aagtaggagt gcaccaattg     600
caaagggaaa agctgaatgg gcagttcgaa tagtacttaa gattcccaca caccatagct     660
tcaaaatgtt tctactcctt ttttactctt ccagattttc tcggactccg cgcatcgccg     720
taccacttca aaacacccaa gcacagcata ctaaatttcc cctctttctt cctctagggt     780
gtcgttaatt acccgtacta aaggtttgga aaagaaaaaa gagaccgcct cgtttctttt     840
tcttcgtcga aaaaggcaat aaaaattttt atcacgtttc tttttcttga aatttttt     900 ttttgatttt tttctctttc gatgacctcc cattgatatt taagttaata acggtcttc     960 aatttctcaa gttcagtttt cattttctt gttctattac aactttttt acttcttgct    1020 cattagaaag aaagcatagc aatctaatct aagttttaat tacaaaatgt ctctctctcc    1080
cgttgttgtt attggaaccg gtttggccgg gctggctgct gccaatgaat tggttaacaa    1140
gtataacatc cctgtaacca tcctcgaaaa ggcttcctcg atcggtggga actctatcaa    1200
ggcctccagt ggtattaacg gtgcttgcac cgagactcaa cgtcacttcc acatcgagga    1260
ctccccacgc ttattgaag atgacaccat caagtctgct aaaggtaaag gtgtccaaga    1320
attaatggct aagttggcca atgattctcc cctggctatt gaatggttga aaacgaattt    1380
tgatttgaaa ttggacctat ggctcaatt gggtggccac tctgtggcaa gaactcacag    1440
atcgtctggg aagttgcctc caggtttcga aattgtttct gccttatcta acaatttgaa    1500
gaaattagct gagactaaac cagagttagt taagattaac ttagacagta aagtcgtaga    1560
catccatgaa aaggatggct ccatttctgc tgtagtgtac gaggacaaga atggcgaaaa    1620
gcacatggtg agtgctaacg atgtcgtttt tgttctgga gggtttggct ttctaagga    1680 aatgcttaaa gaatacgcac ccgaactggt gaacttgcca acaacaaacg gcaacaaac    1740 aactggtgat ggtcaaaggc ttctgcagaa gttaggcgct gatctgattg acatggacca    1800
```

```
aattcaagtt catccaactg ggttcattga tccaaatgac cgtagctcaa gctggaaatt    1860
cttggctgcc gaatccttaa gaggtcttgg tggtatccta ttaaacccta ttaccggtag    1920
aagatttgtc aacgaattga ccacaagaga tgtagtcact gcagctattc aaaaggtttg    1980
tcctcaagag gataacagag cactattggt tatgggcgaa aaaatgtaca cagatttgaa    2040
gaataattta gattttttaca tgttcaagaa acttgtacag aaattgacat tatctcaagt    2100
tgtttctgaa tataatttac caatcactgt cgcccaatta tgcgaggaat tgcaaacata    2160
ctcttccttc actaccaagg ctgatccgtt gggacgtacc gttattctca acgaatttgg    2220
ctctgacgtt actccagaaa ctgtggtttt tattggtgaa gtaacaccgg ttgtccattt    2280
caccatgggt ggtgctagaa tcaatgtcaa ggctcaagtc attggcaaga acgacgaaag    2340
gctactaaaa ggcctgtacg cggccggtga agtttctggc ggtgttcatg cgccaatag     2400 gttgggtggt tcaagtttgt tagaatgcgt tgtctttggg agaaccgcag ctgaatctat    2460
tgccaatgac cgcaagtaaa gagggagagg ataaagagat aaattacgat tttggatttt    2520
aatgatttta taaacaacaa caaccaacca gcctttact  ttatttggca tatacacaag    2580
cttactccat ttcattgatt atctatgtgt atatatataa gtgatgtata acaattatta    2640
ttatacatag ataatatttt tatgatatgt tttttctgag ttttgatatt atttattaca    2700
agttacaagt tacaagttac aagttaccag gaagaattaa ataaaggtaa attgggggaa    2760
atataagcgt atgggcatag atatatatat atatattata gagaacaata agctagggc    2820 aatagggaat taattacaca atccatccga agatcttttc ataatccat  ttcatgtctt    2880 ttccatgggc cttgatataa gcggctcttt cctcgtctag caatttgcct tcttcttcct    2940
ccaaatcgac tggttctttg aaggagacga gatcgacttc ttcggagggg atgagtttgg    3000
tcttgttgcc gccctatacc ttgtctgcct ccccgcgttg cgtcgcggtg catggagccg    3060
ggccacctcg acctgaatgg aagccggcgg cacctcgcta acggattcac cactccaaga    3120
attggagcca atcaattctt gcggagaact gtgaatgcgc aaaccaaccc ttggcagaac    3180
atatccatcg cgtccgccat ctccagcagc cgcacgcggc gcatctcggg cagcgttggg    3240
tcctggccac gggtgcgcat gatcgtgctc ctgtcgttga ggacccggct aggctggcgg    3300
ggttgcctta ctggttagca gaatgaatca ccgatacgcg agcgaacgtg aagcgactgc    3360
tgctgcaaaa cgtctgcgac ctgagcaaca acatgaatgg tcttcggttt ccgtgtttcg    3420
taaagtctgg aaacgcggaa gtcagcgccc tgcaccatta tgttccggat ctgcatcgca    3480
ggatgctgct ggctaccctg tggaacacct acatctgtat taacgaagcg ctggcattga    3540
ccctgagtga ttttttctctg gtcccgccgc atccataccg ccagttgttt accctcacaa    3600
cgttccagta accgggcatg ttcatcatca gtaacccgta tcgtgagcat cctctctcgt    3660
ttcatcggta tcattacccc catgaacaga aattccccct tacacggagg catcaagtga    3720
ccaaacagga aaaaaccgcc cttaacatgg cccgctttat cagaagccag acattaacgc    3780
ttctggagaa actcaacgag ctggacgcgg atgaacaggc agacatctgt gaatcgcttc    3840
acgaccacgc tgatgagctt taccgcagct gcctcgcgcg tttcggtgat gacggtgaaa    3900
acctctgaca catgcagctc ccggagacgg tcacagcttg tctgtaagcg gatgccggga    3960
gcagacaagc ccgtcagggc gcgtcagcgg gtgttggcgg gtgtcggggc gcagccatga    4020
cccagtcacg tagcgatagc ggagtgtata ctggcttaac tatgcggcat cagagcagat    4080
tgtactgaga gtgcaccata tgcggtgtga aataccgcac agatgcgtaa ggagaaaata    4140
```

-continued

```
ccgcatcagg cgctcttccg cttcctcgct cactgactcg ctgcgctcgg tcgttcggct    4200
gcggcgagcg gtatcagctc actcaaaggc ggtaatacgg ttatccacag aatcagggga    4260
taacgcagga agaacatgt gagcaaaagg ccagcaaaag gccaggaacc gtaaaaaggc    4320
cgcgttgctg gcgttttttcc ataggctccg cccccctgac gagcatcaca aaaatcgacg    4380
ctcaagtcag aggtggcgaa acccgacagg actataaaga taccaggcgt ttccccctgg    4440
aagctccctc gtgcgctctc ctgttccgac cctgccgctt accggatacc tgtccgcctt    4500
tctcccttcg ggaagcgtgg cgctttctca tagctcacgc tgtaggtatc tcagttcggt    4560
gtaggtcgtt cgctccaagc tgggctgtgt gcacgaaccc cccgttcagc ccgaccgctg    4620
cgccttatcc ggtaactatc gtcttgagtc aacccggta agacacgact tatcgccact    4680
ggcagcagcc actggtaaca ggattagcag agcgaggtat gtaggcggtg ctacagagtt    4740
cttgaagtgg tggcctaact acggctacac tagaaggaca gtatttggta tctgcgctct    4800
gctgaagcca gttaccttcg gaaaagagt tggtagctct tgatccggca acaaaccac    4860 cgctggtagc ggtggttttt tgtttgcaa gcagcagatt acgcgcagaa aaaaggatc    4920 tcaagaagat cctttgatct tttctacggg gtctgacgct cagtggaacg aaaactcacg    4980
ttaagggatt ttggtcatga gattatcaaa aaggatcttc acctagatcc ttttaaatta    5040
aaaatgaagt tttaaatcaa tctaaagtat atatgagtaa acttggtctg acagttacca    5100
atgcttaatc agtgaggcac ctatctcagc gatctgtcta tttcgttcat ccatagttgc    5160
ctgactcccc gtcgtgtaga taactacgat acgggagggc ttaccatctg gccccagtgc    5220
tgcaatgata ccgcgagacc cacgctcacc ggctccagat ttatcagcaa taaaccagcc    5280
agccggaagg gccgagcgca gaagtggtcc tgcaacttta tccgcctcca tccagtctat    5340
taattgttgc cgggaagcta gagtaagtag ttcgccagtt aatagtttgc gcaacgttgt    5400
tgccattgct gcaggcatcg tggtgtcacg ctcgtcgttt ggtatggctt cattcagctc    5460
cggttcccaa cgatcaaggc gagttacatg atccccccatg ttgtgcaaaa aagcggttag    5520
ctccttcggt cctccgatcg ttgtcagaag taagttggcc gcagtgttat cactcatggt    5580
tatggcagca ctgcataatt ctcttactgt catgccatcc gtaagatgct tttctgtgac    5640
tggtgagtac tcaaccaagt cattctgaga atagtgtatg cggcgaccga gttgctcttg    5700
cccggcgtca acacgggata ataccgcgcc acatagcaga actttaaaag tgctcatcat    5760
tggaaaacgt tcttcggggc gaaaactctc aaggatctta ccgctgttga tccagttc    5820 gatgtaaccc actcgtgcac ccaactgatc ttcagcatct tttactttca ccagcgtttc    5880
tgggtgagca aaaacaggaa ggcaaaatgc cgcaaaaaag gaataagggg cgacacggaa    5940
atgttgaata ctcatactct tccttttca atattattga agcatttatc agggttattg    6000
tctcatgagc ggatacatat ttgaatgtat ttagaaaaat aaacaaatag gggttccgcg    6060
cacatttccc cgaaaagtgc cacctgacgt ctaagaaacc attattatca tgacattaac    6120
ctataaaaat aggcgtatca cgaggccctt tcgtcttcaa gaattctgaa ccagtcctaa    6180
aacgagtaaa taggaccggc aattcttcaa gcaataaaca ggaataccaa ttattaaaag    6240
ataacttagt cagatcgtac aataaagctt gaagaaaaa tgcgccttat caatctttg    6300 ctataaaaaa tggcccaaaa tctcacattg gaagacattt gatgacctca tttctttcaa    6360
tgaagggcct aacggagttg actaatgttg tgggaaattg gagcgataag cgtgcttctg    6420
ccgtggccag gacaacgtat actcatcaga taacagcaat acctgatcac tacttcgcac    6480
tagtttctcg gtactatgca tatgatccaa tatcaaagga aatgatagca ttgaaggatg    6540
```

```
agactaatcc aattgaggag tggcagcata tagaacagct aaagggtagt gctgaaggaa    6600
gcatacgata ccccgcatgg aatgggataa tatcacagga ggtactagac tacctttcat    6660
cctacataaa tagacgcata taagtacgca tttaagcata aacacgcact atgccgttct    6720
tctcatgtat atatatatac aggcaacacg cagatatagg tgcgacgtga acagtgagct    6780
gtatgtgcgc agctcgcgtt gcattttcgg aagcgctcgt tttcggaaac gctttgaagt    6840
tcctattccg aagttcctat tctctagaaa gtataggaac ttcagagcgc ttttgaaaac    6900
caaaagcgct ctgaagacgc actttcaaaa aaccaaaaac gcaccggact gtaacgagct    6960
actaaaatat tgcgaatacc gcttccacaa acattgctca aaagtatctc tttgctatat    7020
atctctgtgc tatatcccta tataacctac ccatccacct ttcgctcctt gaacttgcat    7080
ctaaactcga cctctacatt ttttatgttt atctctagta ttactcttta gacaaaaaaa    7140
ttgtagtaag aactattcat agagtgaatc gaaaacaata cgaaaatgta acatttcct    7200 atacgtagta tatagagaca aaatagaaga aaccgttcat aattttctga ccaatgaaga    7260
atcatcaacg ctatcacttt ctgttcacaa agtatgcgca atccacatcg gtatagaata    7320
taatcgggga tgcctttatc ttgaaaaaat gcacccgcag cttcgctagt aatcagtaaa    7380
cgcgggaagt ggagtcaggc ttttttttatg gaagagaaaa tagacaccaa agtagccttc    7440 ttctaaccttt aacggaccta cagtgcaaaa agttatcaag agactgcatt atagagcgca    7500
caaaggagaa aaaagtaat ctaagatgct ttgttagaaa aatagcgctc tcgggatgca    7560
tttttgtaga acaaaaaaga agtatagatt ctttgttggt aaaatagcgc tctcgcgttg    7620
catttctgtt ctgtaaaaat gcagctcaga ttctttgttt gaaaaattag cgctctcgcg    7680 ttgcatttt gttttacaaa aatgaagcac agattcttcg ttggtaaaat agcgctttcg    7740
cgttgcattt ctgttctgta aaaatgcagc tcagattctt tgtttgaaaa attagcgctc    7800
tcgcgttgca ttttttgttct acaaaatgaa gcacagatgc ttcgttaaca agatatgct    7860 attgaagtgc aagatggaaa cgcagaaaat gaaccgggga tgcgacgtgc aagattacct    7920
atgcaataga tgcaatagtt tctccaggaa ccgaaataca tacattgtct tccgtaaagc    7980
gctagactat atattattat acaggttcaa atatactatc tgtttcaggg aaaactccca    8040
ggttcggatg ttcaaaattc aatgatgggt aacaagtacg atcgtaaatc tgtaaaacag    8100
tttgtcggat attaggctgt atctcctcaa agcgtattcg aatatcattg agaagctgca    8160
gcgtcacatc ggataataat gatggcagcc attgtagaag tgccttttgc atttctagtc    8220
tctttctcgg tctagctagt tttactacat cgcgaagata gaatcttaga tcacactgcc    8280
tttgctgagc tggatcaata gagtaacaaa agagtggtaa ggcctcgtta aaggacaagg    8340
acctgagcgg aagtgtatcg tacagtagac ggagtatact agtatagtct atagtccgtg    8400
gaattctcat gtttgacagc ttatcatcga taagcttttc aattcaattc atcattttttt    8460 ttttattctt tttttgatt tcggtttctt tgaaatttt ttgattcggt aatctccgaa    8520
cagaaggaag aacgaaggaa ggagcacaga cttagattgg tatatatacg catatgtagt    8580
gttgaagaaa catgaaattg cccagtattc ttaacccaac tgcacagaac aaaaacctgc    8640
aggaaacgaa gataaatcat gtcgaaagct acatataagg aacgtgctgc tactcatcct    8700
agtcctgttg ctgccaagct atttaatatc atgcacgaaa agcaaacaaa cttgtgtgct    8760
tcattggatg ttcgtaccac caaggaatta ctggagttag ttgaagcatt aggtcccaaa    8820
atttgtttac taaaaacaca tgtggatatc ttgactgatt tttccatgga gggcacagtt    8880
```

-continued

| | |
|---|---|
| aagccgctaa aggcattatc cgccaagtac aatttttac tcttcgaaga cagaaaattt | 8940 |
| gctgacattg gtaatacagt caaattgcag tactctgcgg gtgtatacag aatagcagaa | 9000 |
| tgggcagaca ttacgaatgc acacggtgtg gtgggcccag gtattgttag cggtttgaag | 9060 |
| caggcggcag aagaagtaac aaaggaacct agaggccttt tgatgttagc agaattgtca | 9120 |
| tgcaagggct ccctatctac tggagaatat actaagggta ctgttgacat tgcgaagagc | 9180 |
| gacaaagatt ttgttatcgg ctttattgct caaagagaca tgggtggaag agatgaaggt | 9240 |
| tacgattggt tgattatgac acccggtgtg ggtttagatg acaagggaga cgcattgggt | 9300 |
| caacagtata gaaccgtgga tgatgtggtc tctacaggat ctgacattat tattgttgga | 9360 |
| agaggactat ttgcaaaggg aagggatgct aaggtagagg gtgaacgtta cagaaaagca | 9420 |
| ggctgggaag catatttgag aagatgcggc cagcaaaact aaaaaactgt attataagta | 9480 |
| aatgcatgta tactaaactc acaaattaga gcttcaattt aattatatca gttattaccc | 9540 |
| gggaatctcg gtcgtaatga tttttataat gacgaaaaaa aaaaaattgg aaagaaaaag | 9600 |
| ctttaatgcg gtagtttatc acagttaaat tgctaacgca gtcaggcacc gtgtatgaaa | 9660 |
| tctaacaatg cgctcatcgt catcctcggc accgtcaccc tggatgctgt aggcataggc | 9720 |
| ttggttatgc cggtactgcc gggcctcttg cgggatatcg tccattccga cagcatcgcc | 9780 |
| agtcactatg gcgtgctgct agcgctatat gcgttgatgc aatttctatg cgcacccgtt | 9840 |
| ctcggagcac tgtccgaccg ctttggccgc cgcccagtcc tgctcgcttc gctacttgga | 9900 |
| gccactatcg actacgcgat catggcgacc acaccgtcc tgtggatcct ctacgccgga | 9960 |
| cgcatcgtgg ccggcatcac cggcccaatg cgaatagcac cagtgagagc accagtaaaa | 10020 |
| gcatacgcat acacatacac acatagagca agcaagcagg ctagcaacca ggaaaggctg | 10080 |
| ccagtgactg ctactgggtg tctaagaacc gtagggcgga ttattgttgc ggtggttggt | 10140 |
| tgcgggtggt tatgcgatgg tacggtgcag aatcgtacgg tgttgggtta tggaattagt | 10200 |
| atgggtatgt gatatgtggt aatatgtgat attgggttat tgtgatttgg aatactgaat | 10260 |
| atcgaatatg ggatatggaa tatggctatg gcatggtatg gtatgggatg ggagtattct | 10320 |
| atttatttt attctggttc ctgcgtttag ggtagggtag gaagaaggtg agtgcttttg | 10380 |
| tatataagtg gagtgtctgg atcagttttg tggattgtga atgttagttt ccccttaat | 10440 |
| gtatatttgt attatttgct tttgagtact caataaccaa gcacaactac tagttttaaa | 10500 |
| ggatccatcc tcttaaacag tacaaatcgc aaagaaaagc tccacaccca aaccaatgcg | 10560 |
| cgttaacaat ggtttgaccc cgcaagaact cgaggcttat ggtatcagtg acgtacatga | 10620 |
| tatcgtttac aacccaagct acgacctgct gtatcaggaa gagctcgatc cgagcctgac | 10680 |
| aggttatgag cgcggggtgt taactaatct gggtgccgtt gccgtcgata ccgggatctt | 10740 |
| caccggtcgt tcaccaaaag ataagtatat cgtccgtgac gataccactc gcgatacttt | 10800 |
| ctggtgggca gacaaaggca aaggtaagaa cgacaacaaa cctctctctc cggaaacctg | 10860 |
| gcagcatctg aaaggcctgg tgaccaggca gctttccggc aaacgtctgt tcgttgtcga | 10920 |
| cgctttctgt ggtgcgaacc cggatactcg tcttccgtc cgtttcatca ccgaagtggc | 10980 |
| ctggcaggcg catttgtca aaacatgtt tattcgcccg agcgatgaag aactggcagg | 11040 |
| tttcaaacca gactttatcg ttatgaacgg cgcgaagtgc actaacccgc agtggaaaga | 11100 |
| acagggtctc aactccgaaa acttcgtggc gtttaacctg accgagcgca tgcagctgat | 11160 |
| tggcggcacc tggtacggcg gcgaaatgaa gaaagggat ttctcgatga tgaactacct | 11220 |
| gctgccgctg aaaggtatcg cttctatgca ctgctccgcc aacgttggtg agaaaggcga | 11280 |

```
tgttgcggtg ttcttcggcc tttccggcac cggtaaaacc acccttttcca ccgacccgaa   11340 acgtcgcctg attggcgatg acgaacacgg ctgggacgat gacggcgtgt ttaacttcga   11400
aggcggctgc tacgcaaaaa ctatcaagct gtcgaaagaa gcggaacctg aaatctacaa   11460
cgctatccgt cgtgatgcgt tgctggaaaa cgtcaccgtg cgtgaagatg cactatcga    11520 ctttgatgat ggttcaaaaa ccgagaacac ccgcgtttct tatccgatct atcacatcga   11580
taacattgtt aagccggttt ccaaagcggg ccacgcgact aaggttatct tcctgactgc   11640
tgatgctttc ggcgtgttgc cgccggtttc tcgcctgact gccgatcaaa cccagtatca   11700
cttcctctct ggcttcaccg ccaaactggc cggtactgag cgtggcatca ccgaaccgac   11760
gccaaccttc tccgcttgct tcggcgcggc attcctgtcg ctgcacccga ctcagtacgc   11820
agaagtgctg gtgaaacgta tgcaggcggc gggcgcgcag gcttatctgg ttaacactgg   11880
ctggaacggc actggcaaac gtatctcgat taaagatacc cgcgccatta tcgacgccat   11940
cctcaacggt tcgctggata atgcagaaac cttcactctg ccgatgttta acctggcgat   12000
cccaaccgaa ctgccgggcg tagacacgaa gattctcgat ccgcgtaaca cctacgcttc   12060
tccggaacag tggcaggaaa aagccgaaac cctggcgaaa ctgtttatcg acaacttcga   12120
taaatacacc gacaccccctg cgggtgccgc gctggtagcg gctggtccga actgtaagg    12180 agattgataa gacttttcta gttgcatatc ttttatattt aaatcttatc tattagttaa   12240
ttttttgtaa tttatcctta tatatagtct ggttattcta aaatatcatt tcagtatcta   12300
aaaattcccc tcttttttca gttatatctt aacaggcgac agtccaaatg ttgatttatc   12360
ccagtccgat tcatcagggt tgtgaagcat tttgtcaatg gtcgaaatca catcagtaat   12420
agtgcctctt acttgcctca tagaatttct ttctcttaac gtcaccgttt ggtcttttat   12480
agtttcgaaa tctatggtga taccaaatgg tgttcccaat tcatcgttac gggcgtattt   12540
tttaccaatt gaagtattgg aatcgtcaat ttaaagtat atctctcttt tacgtaaagc    12600
ctgcgagatc ctcttaagta tagcggggaa gccatcgtta ttcgatattg tcgtaacaaa   12660
tactttgatc ggcgctatct gtaatggaaa cgtacgctgc aggtcgacgg atccccgggt   12720
taattaaggc gcgccagatc tgtttagctt gcctcgtccc cgccgggtca cccggccagc   12780
gacatggagg cccagaatac cctccttgac agtcttgacg tgcgcagctc aggggcatga   12840
tgtgactgtc gcccgtacat ttagcccata catccccatg tataatcatt tgcatccata   12900
cattttgatg ccgcacggc gcgaagcaaa aattacggct cctcgctgca gacctgcgag    12960
cagggaaacg ctcccctcac agacgcgttg aattgtcccc acgccgcgcc cctgtagaga   13020
aatataaaag gttaggattt gccactgagg ttcttctttc atatacttcc ttttaaaatc   13080
ttgctaggat acagttctca catcacatcc gaacataaac aaccatgggt aaggaaaga    13140 ctcacgtttc gaggccgcga ttaaattcca acatggatgc tgatttatat gggtataaat   13200
gggctcgcga taatgtcggg caatcaggtg cgacaatcta tcgattgtat gggaagcccg   13260
atgcgccaga gttgtttctg aaacatggca aaggtagcgt tgccaatgat gttacagatg   13320
agatggtcag actaaactgg ctgacggaat ttatgcctct tccgaccatc aagcatttta   13380
tccgtactcc tgatgatgca tggttactca ccactgcgat ccccggcaaa acagcattcc   13440
aggtattaga agaatatcct gattcaggtg aaaatattgt tgatgcgctg gcagtgttcc   13500
tgcgccggtt gcattcgatt cctgtttgta attgtccttt taacagcgat cgcgtatttc   13560
gtctcgctca ggcgcaatca cgaatgaata acggtttggt tgatgcgagt gattttgatg   13620
```

```
acgagcgtaa tggctggcct gttgaacaag tctggaaaga aatgcataag cttttgccat    13680
tctcaccgga ttcagtcgtc actcatggtg atttctcact tgataacctt attttttgacg   13740 agggaaatt  aataggttgt attgatgttg gacgagtcgg aatcgcagac cgataccagg    13800
atcttgccat cctatggaac tgcctcggtg agttttctcc ttcattacag aaacggcttt    13860
ttcaaaaata tggtattgat aatcctgata tgaataaatt gcagtttcat ttgatgctcg    13920
atgagttttt ctaatcagta ctgacaataa aaagattctt gttttcaaga acttgtcatt    13980
tgtatagttt ttttatattg tagttgttct attttaatca aatgttagcg tgatttatat    14040 ttttttttcgc ctcgacatca tctgcccaga tgcgaagtta agtgcgcaga aagtaatatc   14100
atgcgtcaat cgtatgtgaa tgctggtcgc tatactgctg tcgattcgat actaacgccg    14160
ccatccagtg tcgaaaacga gctcgaattc atcgatcctt cgagattata tctaggaacc    14220
catcaggttg gtggaagatt acccgttcta agacttttca gcttcctcta ttgatgttac    14280
acctggacac cccttttctg gcatccagtt tttaatcttc agtggcatgt gagattctcc    14340
gaaattaatt aaagcaatca cacaattctc tcggatacca cctcggttga aactgacagg    14400
tggtttgtta cgcatgctaa tgcaaaggag cctatatacc tttggctcgg ctgctgtaac    14460
agggaatata aagggcagca taatttagga gtttagtgaa cttgcaacat ttactatttt    14520
cccttcttac gtaaatattt ttcttttttaa ttctaaatca atcttttttca attttttgtt   14580 tgtattcttt tcttgcttaa atctataact acaaaaaaca catacataaa ctaaaaatga    14640
aagtcgcagt cctcggcgct gctggcggta ttggccaggc gcttgcacta ctgttaaaaa    14700
cccaactgcc ttcaggttca gaactctctc tgtatgatat cgctccagtg actcccggtg    14760
tggctgtcga tctgagccat atccctactg ctgtgaaaat caaaggtttt tctggtgaag    14820
atgcgactcc ggcgctggaa ggcgcagatg tcgttcttat ctctgcaggc gtagcgcgta    14880
aaccgggtat ggatcgttcc gacctgttta acgttaacgc cggcatcgtg aaaaacctgg    14940
tacagcaagt tgcgaaaacc tgcccgaaag cgtgcattgg tattatcact aacccggtta    15000
acaccacagt tgcaattgct gctgaagtgc tgaaaaaagc cggtgtttat gacaaaaaca    15060
aactgttcgg cgttaccacg ctggatatca ttcgttccaa caccttttgtt gcggaactga   15120 aaggcaaaca gccaggcgaa gttgaagtgc cggttattgg cggtcactct ggtgttacca    15180
ttctgccgct gctgtcacag gttcctggcg ttagttttac cgagcaggaa gtggctgatc    15240
tgaccaaacg catccagaac gcgggtactg aagtggttga agcgaaggcc ggtggcgggt    15300
ctgcaaccct gtctatgggc caggcagctg cacgttttgg tctgtctctg gttcgtgcac    15360
tgcagggcga acaaggcgtt gtcgaatgtg cctacgttga aggcgacggt cagtacgccc    15420
gtttcttctc tcaaccgctg ctgctgggta aaaacggcgt ggaagagcgt aaatctatcg    15480
gtaccctgag cgcatttgaa cagaacgcgc tggaaggtat gctggatacg ctgaagaaag    15540
atatcgccct gggcgaagag ttcgttaata agtaagatta atataattat ataaaaatat    15600
tatcttcttt tctttatatc tagtgttatg taaaataaat tgatgactac ggaaagcttt    15660
tttatattgt ttcttttttca ttctgagcca cttaaatttc gtgaatgttc ttgtaaggga   15720
cggtagattt acaagtgata caacaaaaag caaggcgctt tttctaataa aaagaagaaa    15780
agcatttaac aattgaacac ctctatatca acgaagaata ttactttgtc tctaaatcct    15840
tgtaaaatgt gtacgatctc tatatgggtt actcataagt gtaccgaaga ctgcattgaa    15900
agtttatgtt ttttcactgg aggcgtcatt ttcgcgttga gaagatgttc ttatccaaat    15960
ttcaactgtt atatagaaga gcaaaaatgc ttgcatttag tcgtgcaatg tatgactttta   16020
```

```
agatttgtga gcaggaagaa aagggagaat cttctaacga taaacccttg aaaaactggg    16080
tagactacgc tatgttgagt tgctacgcag gctgcacaat tacacgagaa tgctcccgcc    16140
taggatttaa ggctaaggga cgtgcaatgc agacgacaga tctaaatgac cgtgtcggtg    16200
aagtgttcgc caaacttttc ggttaacaca tgcagtgatg cacgcgcgat ggtgctaagt    16260
tacatatata tatatatata gccatagtga tgtctaagta acctttatgg tatatttctt    16320
aatgtggaaa gatactagcg cgcgcaccca cacacaagct tcgtcttttc ttgaagaaaa    16380
gaggaagctc gctaaatggg attccacttt ccgttccctg ccagctgatg gaaaaaggtt    16440
agtggaacga tgaagaataa aaagagagat ccactgaggt gaaatttcag ctgacagcga    16500
gtttcatgat cgtgatgaac aatggtaacg agttgtggct gttgccaggg agggtggttc    16560
tcaactttta atgtatggcc aaatcgctac ttgggtttgt tatataacaa agaagaaata    16620
atgaactgat tctcttcctc cttcttgtcc tttcttaatt ctgttgtaat taccttcctt    16680
tgtaattttt tttgtaatta ttcttcttaa taatccaaac aaacacacat attacaataa    16740
tgaatacagt acgcagcgaa aaagattcga tgggggcgat tgatgtcccg gcagataagc    16800
tgtggggcgc acaaactcaa cgctcgctgg agcatttccg catttcgacg gagaaaatgc    16860
ccacctcact gattcatgcg ctggcgctaa ccaagcgcgc agcggcaaaa gttaatgaag    16920
atttaggctt gttgtctgaa gagaaagcga gcgccattcg gcaggcggcg gatgaagtac    16980
tggcaggaca gcatgacgac gaattcccgc tggctatctg gcagaccggc tccggcacgc    17040
aaagtaacat gaacatgaac gaagtgctgg ctaaccgggc cagtgaatta ctcggcggcg    17100
tgcgcgggat ggaacgtaaa gttcacccta acgacgacgt gaacaaaagc caaagttcca    17160
acgatgtctt tccgacggcg atgcacgttg cggcgctgct ggcgctgcgc aagcaactca    17220
ttccgcagct taaaaccctg acacagacgc tgagtgaaaa atcgcgtgca tttgccgata    17280
tcgtcaaaat cggtcgaacc cacttgcagg acgccacgcc gctaacactg gggcaggaga    17340
tttccggctg ggtagcgatg ctcgagtata atctcaaaca tatcgaatac agcctgcctc    17400
acgtagcgga actggctctt ggcggtacag cggtgggtac tggactaaat acccatccgg    17460
agtatgcgcg tcgcgtagca gatgaactgg cagtcattac ctgtgcaccg tttgttaccg    17520
cgccgaacaa atttgaagcg ctggcgacct gtgatgctct ggttcaggcg cacggcgcgt    17580
tgaaagggtt ggctgcgtca ctgatgaaaa tcgccaatga tgtccgctgg ctggcctctg    17640
gcccgcgctg cggaattggt gaaatctcaa tcccggaaaa tgagccgggc agctcaatca    17700
tgccggggaa agtgaatcca acacagtgtg aggcattaac catgctctgc tgtcaggtga    17760
tggggaacga cgtggcgatc aacatggggg gcgcttccgg taactttgaa ctgaacgtct    17820
tccgtccaat ggtgatccac aatttcctgc aatcggtgcg cttgctggca gatggcatgg    17880
aaagttttaa caaacactgc gcagtgggta ttgaaccgaa tcgtgagcga atcaatcaat    17940
tactcaatga atcgctgatg ctggtgactg cgcttaacac ccacattggt tatgacaaag    18000
ccgcggagat cgccaaaaaa gcgcataaag aagggctgac cttaaaagct gcggcccttg    18060
cgctggggta tctagcgaa gccgagtttg acagctgggt acggccagaa cagatggtcg    18120
gcagtatgaa agccgggcgt taaa                                           18144
```